(12) United States Patent
Goldshmidt et al.

(10) Patent No.: US 6,677,137 B2
(45) Date of Patent: Jan. 13, 2004

(54) AVIAN AND REPTILE DERIVED POLYNUCLEOTIDE ENCODING A POLYPEPTIDE HAVING HEPARANASE ACTIVITY

(75) Inventors: Orit Goldshmidt, Jerusalem (IL); Iris Pecker, Rishon LeZion (IL); Israel Vlodavsky, Mevaseret Zion (IL); Israel Michal, Ashkelon (IL); Eyal Zcharia, Jerusalem (IL)

(73) Assignees: Insight Strategy & Marketing Ltd., Rehovot (IL); Hadesit Medical Research Services and Development Ltd., Jerusalem (IL)

( * ) Notice: Subject to any disclaimer, the term of this patent is extended or adjusted under 35 U.S.C. 154(b) by 106 days.

(21) Appl. No.: 09/930,218

(22) Filed: Aug. 16, 2001

(65) Prior Publication Data

US 2002/0034810 A1 Mar. 21, 2002

Related U.S. Application Data

(63) Continuation-in-part of application No. 09/666,390, filed on Sep. 20, 2000, now abandoned.

(51) Int. Cl.$^7$ ............ C12P 21/06; C12N 9/00; C12N 9/24; C12N 9/26; C12N 9/40; C12N 9/42; C12N 9/44; C12N 1/20; C12N 15/00; C07K 1/00; C07K 14/00; C07K 17/00

(52) U.S. Cl. .............. 435/69.1; 435/183; 435/201; 435/202; 435/203; 435/204; 435/205; 435/206; 435/207; 435/208; 435/209; 435/210; 435/211; 435/325; 435/349; 435/252.3; 435/320.1; 530/350

(58) Field of Search .............. 435/69.1, 183, 435/200–211, 195, 325, 349, 252.3, 320.1; 530/350; 536/23.1

(56) References Cited

FOREIGN PATENT DOCUMENTS

WO    WO 99/21975    * 5/1999

OTHER PUBLICATIONS

Freeman et al., Database Genseq, Accession No. AAY17082, Jul. 21, 1999.*

Tirunagaru et al. GenBank Database Accession No. AI980994, Jul. 10, 2000.*

Freeman et al. GenBank Database Accession No. AAX37259, Jul. 21, 1999.*

Vlodavsky et al., Mammalian Heparanase: Gene Cloning, Expression and Function in Tumor Progression and Metastasis, Nature Medicine, vol. 5, No. 7, Jul. 1999, pp 793–802.

Kussie, et al., Cloning and Functional Expression of a Human Heparanase Gene, Biochemical and Biophysical Research Communications, vol. 261, 1999, pp 183–187.

Huleit, Cloning of Mammalian Heparanase, an Important Enzyme in Tumor Invasion and Metastasis, Nature Medicine, vol. 5, No. 7, Jul. 1999, pp. 803–809.

Toyoshima et al., Human Heparanase, Purification, Characterization, Cloning and Express, The Journal of Biological Chemistry, vol. 274, No. 34, Aug. 20, 1999, pp. 24153–24160.

Fairbanks et al., Processing of the Human Heparanase Precursor and Evidence that the Active Enzyme is a Heterodimer, The Journal of Biological Chemistry, vol. 274, No. 42, Oct. 15, 1999, pp. 29587–29590.

Friedmann, et al., Expression of Heparanase in Normal, Dysplastic, and Neoplastic Human Colonic Mucosa and Stroma, American Journal of Pathology, vol. 157, No. 4, Oct. 2000, pp. 1167–1175.

* cited by examiner

Primary Examiner—Rebecca E. Prouty
Assistant Examiner—Manjunath N. Rho
(74) Attorney, Agent, or Firm—G. E. Ehrlich (1995) Ltd.

(57) ABSTRACT

Avian and reptile derived heparanase and nucleic acids encoding same.

16 Claims, 14 Drawing Sheets

(1 of 14 Drawing Sheet(s) Filed in Color)

|  | | Seq ID No: |
|---|---|---|
| mouse | -MLR------LLLLWLWGPLGALAQGAPAGTAPTDDVVDLEFYTKRPLRSVSPSFLSIT | 1 |
| rat | -MLRP-----LLLLWLWGRLRALTQGTPAGTAPTKDVVDLEFYTKRLFQSVSPSFLSIT | 2 |
| human | -MLRP-----LLLLWLWGRLRALTQGTPAGTAPTKDVVDLEFYTKRLFQSVSPSFLSIT | 3 |
| chicken | MLLRSKPALPPPLMLLLGPLGPLSPGALPRPAQAQDVVDLDFFTQEPLHLVSPSFLSVT | 4 |
|  | --------------MLVLILLLVLLAVPP--------RR-TAELQLGLREPIGAVSPAFLSLT |  |
|  | * : : * *** : : . .:*: .: *.** .*.**: :* |  |

```
                10         20         30         40         50         60
                 |          |          |          |          |          |
```

```
                 70         80         90        100        110        120
                  |          |          |          |          |          |
mouse    IDASLATDPRFLTFLGSPRLRALARGLSPAYLRFGGTKTDFLIFDPKEPTSEERSYWKS
rat      IDASLATDPRFLTFLGSPRLRALARGLSPAYLRFGGTKTDFLIFDPNKEPTSEERSYWQS
human    IDANLATDPRFLILLGSPKLRTLARGLSPAYLRFGGTKTDFLIFDPKKESTFEERSYWQS
chicken  LDASLARDPRFVALLRHFKLHTLASGLSPGFLRFGGTSTDFLIFNPKDSTWEEKVLSEF
         :** **:***:: : *:: : :** :******:****.*::*  *: .:  :
```

```
                130        140        150        160        170        180
                  |          |          |          |          |          |
mouse    QVNHDICRSEPVSAAVIRKLQVEWPFQELLLLREQYQKEFKNSTYSRSSVDMLYSFAKCS
rat      QDNNDICGSERVSADVLRKLQMEWPFQELLLLREQYQREFKNSTYSRSSVDMLYSFAKCS
human    QVNQDICKYGSIPPDVEEKLRLEWPYQEQLLLREHYQKKFKNSTYSRSSVDVLYTFANCS
chicken  QAK-DVCEAWPSFAVVPKLLLTQWPLQEKLLLAEHSWKKHKNTTITRSTLDILHTFASSS
         *   *:*    .  : :*:  * *: * :**  : ::: :** *:*::::  ..*  *
```

```
                190        200        210        220        230        240
                  |          |          |          |          |          |
mouse    GLDLIFGLNALLRTPDLRWNSSNAQLLLDYCSSKGYNISWELGNEPNSFWKKAHILIDGL
rat      RLDLIFGLNALLRTPDLRWNSSNAQLLLNYCSSKGYNISWELGNEPNSFWKKAQISIDGL
human    GLDLIFGLNALLRTADLQWNSSNAQLLLDYCSSKGYNISWELGNEPNSFLKKADIFINGS
chicken  GFRLVFGLNALLRRAGLQWDSSNAKQLLGYCAQRSYNISWELGNEPNSFRKKSGICIDGF
         * **********: *:* ****: ** ** :.*************** :*: :    
```

Fig. 1a

```
              250         260         270         280         290         300
               |           |           |           |           |           |
mouse     QLGEDFVELHKLLQRS-AFQNAKLYGPDIGQPRGKTVKLLRSFLKAGGEVIDSLTWHHYY
rat       QLGEDFVELHKLLQKS-AFQNAKLYGPDIGQPRGKTVKLLRSFLKAGGEVIDSLTWHHYY
human     QLGEDYIQLHKLLRKS-TFKNAKLYGPDVGQPRRKTAKMLKSFLKAGGEVIDSVTWHHYY
chicken   QLGRDFVHLRQLLSQHPLYRHAELYGLDVGQPRKHTQHLLRSFMKSGGKAIDSVTWHHYY
          ***.*:.*:::.*::   :  ::.****.:.***:*.*. *:.**:*.**:***.*****

310         320         330         340         350         360
               |           |           |           |           |           |
mouse     LNGRIATKEDFLSSDALDTFILSVQKILKVTKEITPGKKVWLGETSSAYGGGAPLLSNTF
rat       LNGRVATKEDFLSSDVLDTFILSVQKILKVTKEMTPGKKVWLGETSSAYGGGAPLLSNTF
human     LNGRTATREDFLNPDVLDIFISSVQKVFQVVESTRPGKKVWLGETGSAYGGGAPLLSDTF
chicken   VNGRSATREDFLSPEVLDSFATAIHDVLGIVEATVPGKKVWLGETGSAYGGGAPQLSNTY
          :***:**:****.. :** *  : ::.: :  . **********.******* **:*

370         380         390         400         410         420
               |           |           |           |           |           |
mouse     AAGFMWLDKLGLSAQMGIEVVMRQVFFGAGNYHLVDENFEPLPDYWLSLLFKKLVGPRVL
rat       AAGFMWLDKLGLSAQLGIEVVMRQVFFGAGNYHLVDENFEPLPDYWLSLLFKKLVGPKVL
human     AAGFMWLDKLGLSARMGIEVVMRQVFFGAGNYHLVDENFDPLPDYWLSLLFKKLVGTKVL
chicken   VAGFMWLDKLGLAARRGIDVVMRQVSFGAGSYHLVDAGFKPLPDYWLSLLYKRLVGTRVL
          .***********:*: **:****** ****.*****  *.********** *:***::**
```

Fig. 1a (Continued)

```
                 430       440       450       460       470       480
                   |         |         |         |         |         |
mouse    LSRVKGPDRSKLRVYLHCTNVYHPRYQEGDLTLYVLNLHNVTKHLKVPPPLFRKPVDTYL
rat      MSRVKGPDRSKLRVYLHCTNVYHPRYREGDLTLYVLNLHNVTKHLKLPPPMFSRPVDKYL
human    MASVQGSKRRKLRVYLHCTNTDNPRYKEGDLTLYAINLHNVTKYLRLPYPFSNKQVDKYL
chicken  QASVEQADARRPRVYLHCTNPRHPKYREGDVTLFALNLSNVTQSLQLPKQLWSKSVDQYL
           *:  .  : ..****** .*.  ***  **.:.* :*:.** *.:   .   .  *

490       500       510       520       530       540
                   |         |         |         |         |         |
mouse    LKPSGPDGLLSKSVQLNGQILKMVDEQTLPALTEKPLPAGSALSLPAFSYGFFVIRNAKI
rat      LKPFGSDGLLSKSVQLNGQTLKMVDEQTLPALTEKPLPAGSSLSVPAFSYGFFVIRNAKI
human    LRPLGPHGLLSKSVQLNGLTLKMVDDQTLPPLMEKPLRPGSSLGLPAFSYSFFVIRNAKV
chicken  LLPHGKDSILSREVQLNGRLLQMVDDETLPALHEMALAPGSTLGLPAFSYGFYVIRNAKA
          * *   . :**:.****  : ***::.**.*    .*.**: *.****..*:******.

mouse    AACI
rat      AACI
human    AACI
chicken  IACI
          ***
```

Fig. 1a (Continued)

```
                                              A AGG TGA GAA GGA GGA GGA AGG      23 SEQ ID NO:10
ATG CTG GTG CTG CTG CTC GTG CTG CTC GCT GTG CCG CCG              67   SEQ ID NO:4
Met Leu Val Leu Leu Leu Val Leu Leu Ala Val Pro Pro
                      5                          10                    15

AGG CGG ACG GCA GAG CTG CAG CTG GGG CTG CGG GAA CCC ATC GGG      112
Arg Arg Thr Ala Glu Leu Gln Leu Gly Leu Arg Glu Pro Ile Gly
                     20                          25                    30

GCG GTA AGC CCA GCC TTC CTC TCT CTT ACA CTG GAC GCC AGC TTG      157
Ala Val Ser Pro Ala Phe Leu Ser Leu Thr Leu Asp Ala Ser Leu
                     35                          40                    45

GCC CGT GAC CCG CGC TTT GTT GCC CTG CTC AGA CAC CCC AAG CTG      202
Ala Arg Asp Pro Arg Phe Val Ala Leu Leu Arg His Pro Lys Leu
                     50                          55                    60

CAC ACT CTG GCC AGT GGG CTC TCC CCA GGC TTC CTC AGG TTT GGT      247
His Thr Leu Ala Ser Gly Leu Ser Pro Gly Phe Leu Arg Phe Gly
                     65                          70                    75

GGC ACC AGT ACA GAT TTC CTG ATC TTC AAT CCC AAC AAA GAT TCA      292
Gly Thr Ser Thr Asp Phe Leu Ile Phe Asn Pro Asn Lys Asp Ser
                     80                          85                    90
```

Fig. 1b

```
ACT TGG GAA GAG AAA GTC TTG TCG GAA TTT CAG GCC AAG GAT GTG   337
Thr Trp Glu Glu Lys Val Leu Ser Glu Phe Gln Ala Lys Asp Val
             95                    100                   105

TGT GAA GCG TGG CCC AGC TTT GCT GTG GTT CCA AAG CTG CTC CTC   382
Cys Glu Ala Trp Pro Ser Phe Ala Val Val Pro Lys Leu Leu Leu
             110                   115                   120

ACC CAG TGG CCC CTC CAG GAG AAA CTG CTC CTC GCT GAA CAT TCC   427
Thr Gln Trp Pro Leu Gln Glu Lys Leu Leu Leu Ala Glu His Ser
             125                   130                   135

TGG AAA AAG CAC AAA AAC ACC ACC ATT ACA AGG AGC ACG CTG GAC   472
Trp Lys Lys His Lys Asn Thr Thr Ile Thr Arg Ser Thr Leu Asp
             140                   145                   150

ATC CTC CAC ACG TTC GCC AGC AGC TCA GGC TTC CGC CTG GTG TTT   517
Ile Leu His Thr Phe Ala Ser Ser Ser Gly Phe Arg Leu Val Phe
             155                   160                   165

GGG CTG AAC GCA CTG CTG CGC AGG GCT GGC CTG CAG TGG GAC AGC   562
Gly Leu Asn Ala Leu Leu Arg Arg Ala Gly Leu Gln Trp Asp Ser
             170                   175                   180
```

Fig. 1b (Continued)

```
TCC AAC GCC AAG CAG CTG CTG GGC TAC TGT GCA CAG CGC AGC TAC    607
Ser Asn Ala Lys Gln Leu Leu Gly Tyr Cys Ala Gln Arg Ser Tyr
                185                 190                 195

AAC ATC TCC TGG GAG CTG GGT AAT GAG CCC AAC AGC TTC AGG AAG    652
Asn Ile Ser Trp Glu Leu Gly Asn Glu Pro Asn Ser Phe Arg Lys
                200                 205                 210

AAG TCG GGC ATC TGC ATC GAT GGC TTC CAG TTG GGA CGT GAT TTC    697
Lys Ser Gly Ile Cys Ile Asp Gly Phe Gln Leu Gly Arg Asp Phe
                215                 220                 225

GTC CAC CTG CGG CAG CTC CTG AGC CAG CAC CCC CTG TAC CGA CAC    742
Val His Leu Arg Gln Leu Leu Ser Gln His Pro Leu Tyr Arg His
                230                 235                 240

GCT GAG CTG TAC GGC CTC GAC GTG GGG CAG CCC CGC AAG CAC ACC    787
Ala Glu Leu Tyr Gly Leu Asp Val Gly Gln Pro Arg Lys His Thr
                245                 250                 255

CAG CAC CTG CTC AGA AGC TTC ATG AAA TCT GGA GGG AAG GCG ATT    832
Gln His Leu Leu Arg Ser Phe Met Lys Ser Gly Gly Lys Ala Ile
                260                 265                 270
```

Fig. 1b (Continued)

```
GAC TCG GTC ACC TGG CAC CAC TAC TAT GTG AAT GGC CGA AGT GCA    877
Asp Ser Val Thr Trp His His Tyr Tyr Val Asn Gly Arg Ser Ala
                275                 280                 285

ACG AGG GAG GAT TTC CTG AGC CCT GAA GTG CTG GAC TCC TTT GCC    922
Thr Arg Glu Asp Phe Leu Ser Pro Glu Val Leu Asp Ser Phe Ala
                290                 295                 300

ACT GCC ATA CAC GAT GTC CTG GGG ATC GTG GAA GCA ACG GTG CCC    967
Thr Ala Ile His Asp Val Leu Gly Ile Val Glu Ala Thr Val Pro
                305                 310                 315

GGC AAG AAG GTA TGG CTG GGT GAG ACC CGG TCG GCC TAC GGC GGG    1012
Gly Lys Lys Val Trp Leu Gly Glu Thr Arg Ser Ala Tyr Gly Gly
                320                 325                 330

GGG GCC CCC CAG CTC TCC AAC ACC TAT GTG GCC GGC TTC ATG TGG    1057
Gly Ala Pro Gln Leu Ser Asn Thr Tyr Val Ala Gly Phe Met Trp
                335                 340                 345
```

Fig. 1b (Continued)

```
CTG GAC AAG CTG GGG TTG GCG GCT CGG CGT GGC ATT GAT GTG GTG   1102
Leu Asp Lys Leu Gly Leu Ala Ala Arg Arg Gly Ile Asp Val Val
             350                 355                 360

ATG AGG CAG GTC TCC TTT GGT GCT GGC AGC TAT CAC CTG GTG GAT   1147
Met Arg Gln Val Ser Phe Gly Ala Gly Ser Tyr His Leu Val Asp
             365                 370                 375

GCC GGC TTC AAG CCC TTG CCG GAC TAC TGG CTG TCA CTG CTA TAC   1192
Ala Gly Phe Lys Pro Leu Pro Asp Tyr Trp Leu Ser Leu Leu Tyr
             380                 385                 390

AAG AGG CTG GTG GGC ACC CGG GTA CTA CAG GCC AGC GTG GAG CAA   1237
Lys Arg Leu Val Gly Thr Arg Val Leu Gln Ala Ser Val Gln
             395                 400                 405

GCG GAT GCG CGG CGC CCG CGG GTC TAC CTG CAC TGC ACC AAC CCC   1282
Ala Asp Ala Arg Arg Pro Arg Val Tyr Leu His Cys Thr Asn Pro
             410                 415                 420

CGG CAC CCC AAA TAC CGG GAA GGG GAT GTG ACA CTG TTT GCC TTG   1327
Arg His Pro Lys Tyr Arg Glu Gly Asp Val Thr Leu Phe Ala Leu
             425                 430                 435
```

Fig. 1b (Continued)

```
AAC CTC TCC AAC GTG ACC CAG AGC TTG CAG CTG CCT AAG CAG TTG   1372
Asn Leu Ser Asn Val Thr Gln Ser Leu Gln Leu Pro Lys Gln Leu
            440                 445                 450

TGG AGT AAG AGT GTG GAT CAG TAC CTG CTG CTG CCC CAC GGC AAG   1417
Trp Ser Lys Ser Val Asp Gln Tyr Leu Leu Leu Pro His Gly Lys
            455                 460                 465

GAC AGC ATC CTG TCC AGA GAG GTG CAG CTG AAT GGC CGC CTA CTG   1462
Asp Ser Ile Leu Ser Arg Glu Val Gln Leu Asn Gly Arg Leu Leu
            470                 475                 480

CAG ATG GTG GAC GAT GAG ACA CTC CCC GCG CTG CAC GAG ATG GCC   1507
Gln Met Val Asp Asp Glu Thr Leu Pro Ala Leu His Glu Met Ala
            485                 490                 495

CTT GCC CCT GGC AGC ACG CTC GGC CTG CCA GCC TTC TCT TAC GGT   1552
Leu Ala Pro Gly Ser Thr Leu Gly Leu Pro Ala Phe Ser Tyr Gly
            500                 505                 510

TTC TAC GTG ATC AGG AAC GCT AAG GCT ATT GCT TGC ATT TGA GCA   1597
Phe Tyr Val Ile Arg Asn Ala Lys Ala Ile Ala Cys Ile
            515                 520         523
```

Fig. 1b (Continued)

SEQUENCE LISTING

<160> NUMBER OF SEQ ID NOS: 16

<210> SEQ ID NO 1
<211> LENGTH: 535
<212> TYPE: PRT
<213> ORGANISM: Mus musculus

<400> SEQUENCE: 1

```
Met Leu Arg Leu Leu Leu Leu Trp Leu Trp Gly Pro Leu Gly Ala Leu
1               5                   10                  15

Ala Gln Gly Ala Pro Ala Gly Thr Ala Pro Thr Asp Asp Val Val Asp
            20                  25                  30

Leu Glu Phe Tyr Thr Lys Arg Pro Leu Arg Ser Val Ser Pro Ser Phe
        35                  40                  45

Leu Ser Ile Thr Ile Asp Ala Ser Leu Ala Thr Asp Pro Arg Phe Leu
    50                  55                  60

Thr Phe Leu Gly Ser Pro Arg Leu Arg Ala Leu Ala Arg Gly Leu Ser
65                  70                  75                  80

Pro Ala Tyr Leu Arg Phe Gly Gly Thr Lys Thr Asp Phe Leu Ile Phe
                85                  90                  95

Asp Pro Asp Lys Glu Pro Thr Ser Glu Glu Arg Ser Tyr Trp Lys Ser
            100                 105                 110

Gln Val Asn His Asp Ile Cys Arg Ser Glu Pro Val Ser Ala Ala Val
        115                 120                 125

Leu Arg Lys Leu Gln Val Glu Trp Pro Phe Gln Glu Leu Leu Leu Leu
    130                 135                 140

Arg Glu Gln Tyr Gln Lys Glu Phe Lys Asn Ser Thr Tyr Ser Arg Ser
145                 150                 155                 160

Ser Val Asp Met Leu Tyr Ser Phe Ala Lys Cys Ser Gly Leu Asp Leu
                165                 170                 175

Ile Phe Gly Leu Asn Ala Leu Leu Arg Thr Pro Asp Leu Arg Trp Asn
            180                 185                 190

Ser Ser Asn Ala Gln Leu Leu Leu Asp Tyr Cys Ser Ser Lys Gly Tyr
        195                 200                 205

Asn Ile Ser Trp Glu Leu Gly Asn Glu Pro Asn Ser Phe Trp Lys Lys
    210                 215                 220

Ala His Ile Leu Ile Asp Gly Leu Gln Leu Gly Glu Asp Phe Val Glu
225                 230                 235                 240

Leu His Lys Leu Leu Gln Arg Ser Ala Phe Gln Asn Ala Lys Leu Tyr
                245                 250                 255

Gly Pro Asp Ile Gly Gln Pro Arg Gly Lys Thr Val Lys Leu Leu Arg
            260                 265                 270

Ser Phe Leu Lys Ala Gly Gly Glu Val Ile Asp Ser Leu Thr Trp His
        275                 280                 285

His Tyr Tyr Leu Asn Gly Arg Ile Ala Thr Lys Glu Asp Phe Leu Ser
    290                 295                 300

Ser Asp Ala Leu Asp Thr Phe Ile Leu Ser Val Gln Lys Ile Leu Lys
305                 310                 315                 320

Val Thr Lys Glu Ile Thr Pro Gly Lys Lys Val Trp Leu Gly Glu Thr
                325                 330                 335

Ser Ser Ala Tyr Gly Gly Gly Ala Pro Leu Leu Ser Asn Thr Phe Ala
            340                 345                 350

Ala Gly Phe Met Trp Leu Asp Lys Leu Gly Leu Ser Ala Gln Met Gly
```

```
                355                 360                 365
Ile Glu Val Val Met Arg Gln Val Phe Phe Gly Ala Gly Asn Tyr His
            370                 375                 380
Leu Val Asp Glu Asn Phe Glu Pro Leu Pro Asp Tyr Trp Leu Ser Leu
385                 390                 395                 400
Leu Phe Lys Lys Leu Val Gly Pro Arg Val Leu Leu Ser Arg Val Lys
                405                 410                 415
Gly Pro Asp Arg Ser Lys Leu Arg Val Tyr Leu His Cys Thr Asn Val
                420                 425                 430
Tyr His Pro Arg Tyr Gln Glu Gly Asp Leu Thr Leu Tyr Val Leu Asn
                435                 440                 445
Leu His Asn Val Thr Lys His Leu Lys Val Pro Pro Leu Phe Arg
            450                 455                 460
Lys Pro Val Asp Thr Tyr Leu Leu Lys Pro Ser Gly Pro Asp Gly Leu
465                 470                 475                 480
Leu Ser Lys Ser Val Gln Leu Asn Gly Gln Ile Leu Lys Met Val Asp
                485                 490                 495
Glu Gln Thr Leu Pro Ala Leu Thr Glu Lys Pro Leu Pro Ala Gly Ser
            500                 505                 510
Ala Leu Ser Leu Pro Ala Phe Ser Tyr Gly Phe Phe Val Ile Arg Asn
                515                 520                 525
Ala Lys Ile Ala Ala Cys Ile
            530                 535

<210> SEQ ID NO 2
<211> LENGTH: 536
<212> TYPE: PRT
<213> ORGANISM: Rattus rattus

<400> SEQUENCE: 2

Met Leu Arg Pro Leu Leu Leu Trp Leu Trp Gly Arg Leu Arg Ala
1               5                   10                  15

Leu Thr Gln Gly Thr Pro Ala Gly Thr Ala Pro Thr Lys Asp Val Val
            20                  25                  30

Asp Leu Glu Phe Tyr Thr Lys Arg Leu Phe Gln Ser Val Ser Pro Ser
        35                  40                  45

Phe Leu Ser Ile Thr Ile Asp Ala Ser Leu Ala Thr Asp Pro Arg Phe
    50                  55                  60

Leu Thr Phe Leu Gly Ser Pro Arg Leu Arg Ala Leu Ala Arg Gly Leu
65                  70                  75                  80

Ser Pro Ala Tyr Leu Arg Phe Gly Gly Thr Lys Thr Asp Phe Leu Ile
                85                  90                  95

Phe Asp Pro Asn Lys Glu Pro Thr Ser Glu Glu Arg Ser Tyr Trp Gln
            100                 105                 110

Ser Gln Asp Asn Asn Asp Ile Cys Gly Ser Glu Arg Val Ser Ala Asp
        115                 120                 125

Val Leu Arg Lys Leu Gln Met Glu Trp Pro Gln Glu Leu Leu Leu
    130                 135                 140

Leu Arg Glu Gln Tyr Gln Arg Glu Phe Lys Asn Ser Thr Tyr Ser Arg
145                 150                 155                 160

Ser Ser Val Asp Met Leu Tyr Ser Phe Ala Lys Cys Ser Arg Leu Asp
                165                 170                 175

Leu Ile Phe Gly Leu Asn Ala Leu Leu Arg Thr Pro Asp Leu Arg Trp
            180                 185                 190
```

```
Asn Ser Ser Asn Ala Gln Leu Leu Asn Tyr Cys Ser Ser Lys Gly
        195                 200                 205

Tyr Asn Ile Ser Trp Glu Leu Gly Asn Glu Pro Asn Ser Phe Trp Lys
    210                 215                 220

Lys Ala Gln Ile Ser Ile Asp Gly Leu Gln Leu Gly Glu Asp Phe Val
225                 230                 235                 240

Glu Leu His Lys Leu Leu Gln Lys Ser Ala Phe Gln Asn Ala Lys Leu
            245                 250                 255

Tyr Gly Pro Asp Ile Gly Gln Pro Arg Gly Lys Thr Val Lys Leu Leu
            260                 265                 270

Arg Ser Phe Leu Lys Ala Gly Gly Glu Val Ile Asp Ser Leu Thr Trp
            275                 280                 285

His His Tyr Tyr Leu Asn Gly Arg Val Ala Thr Lys Glu Asp Phe Leu
            290                 295                 300

Ser Ser Asp Val Leu Asp Thr Phe Ile Leu Ser Val Gln Lys Ile Leu
305                 310                 315                 320

Lys Val Thr Lys Glu Met Thr Pro Gly Lys Lys Val Trp Leu Gly Glu
                325                 330                 335

Thr Ser Ser Ala Tyr Gly Gly Ala Pro Leu Leu Ser Asn Thr Phe
            340                 345                 350

Ala Ala Gly Phe Met Trp Leu Asp Lys Leu Gly Leu Ser Ala Gln Leu
            355                 360                 365

Gly Ile Glu Val Val Met Arg Gln Val Phe Phe Gly Ala Gly Asn Tyr
    370                 375                 380

His Leu Val Asp Glu Asn Phe Glu Pro Leu Pro Asp Tyr Trp Leu Ser
385                 390                 395                 400

Leu Leu Phe Lys Lys Leu Val Gly Pro Lys Val Leu Met Ser Arg Val
                405                 410                 415

Lys Gly Pro Asp Arg Ser Lys Leu Arg Val Tyr Leu His Cys Thr Asn
                420                 425                 430

Val Tyr His Pro Arg Tyr Arg Glu Gly Asp Leu Thr Leu Tyr Val Leu
            435                 440                 445

Asn Leu His Asn Val Thr Lys His Leu Lys Leu Pro Pro Met Phe
    450                 455                 460

Ser Arg Pro Val Asp Lys Tyr Leu Leu Lys Pro Phe Gly Ser Asp Gly
465                 470                 475                 480

Leu Leu Ser Lys Ser Val Gln Leu Asn Gly Gln Thr Leu Lys Met Val
            485                 490                 495

Asp Glu Gln Thr Leu Pro Ala Leu Thr Glu Lys Pro Leu Pro Ala Gly
                500                 505                 510

Ser Ser Leu Ser Val Pro Ala Phe Ser Tyr Gly Phe Phe Val Ile Arg
            515                 520                 525

Asn Ala Lys Ile Ala Ala Cys Ile
            530                 535

<210> SEQ ID NO 3
<211> LENGTH: 543
<212> TYPE: PRT
<213> ORGANISM: Homo sapiens

<400> SEQUENCE: 3

Met Leu Leu Arg Ser Lys Pro Ala Leu Pro Pro Pro Leu Met Leu Leu
1               5                   10                  15

Leu Leu Gly Pro Leu Gly Pro Leu Ser Pro Gly Ala Leu Pro Arg Pro
            20                  25                  30
```

-continued

```
Ala Gln Ala Gln Asp Val Val Asp Leu Asp Phe Phe Thr Gln Glu Pro
         35                  40                  45

Leu His Leu Val Ser Pro Ser Phe Leu Ser Val Thr Ile Asp Ala Asn
 50                  55                  60

Leu Ala Thr Asp Pro Arg Phe Leu Ile Leu Leu Gly Ser Pro Lys Leu
 65                  70                  75                  80

Arg Thr Leu Ala Arg Gly Leu Ser Pro Ala Tyr Leu Arg Phe Gly Gly
                 85                  90                  95

Thr Lys Thr Asp Phe Leu Ile Phe Asp Pro Lys Lys Glu Ser Thr Phe
             100                 105                 110

Glu Glu Arg Ser Tyr Trp Gln Ser Gln Val Asn Gln Asp Ile Cys Lys
         115                 120                 125

Tyr Gly Ser Ile Pro Pro Asp Val Glu Glu Lys Leu Arg Leu Glu Trp
 130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
    210                 215                 220

Glu Pro Asn Ser Phe Leu Lys Lys Ala Asp Ile Phe Ile Asn Gly Ser
225                 230                 235                 240

Gln Leu Gly Glu Asp Tyr Ile Gln Leu His Lys Leu Leu Arg Lys Ser
                245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
    290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
        355                 360                 365

Leu Gly Leu Ser Ala Arg Met Gly Ile Glu Val Val Met Arg Gln Val
    370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445
```

-continued

```
Asp Leu Thr Leu Tyr Ala Ile Asn Leu His Asn Val Thr Lys Tyr Leu
    450                 455                 460

Arg Leu Pro Tyr Pro Phe Ser Asn Lys Gln Val Asp Lys Tyr Leu Leu
465                 470                 475                 480

Arg Pro Leu Gly Pro His Gly Leu Leu Ser Lys Ser Val Gln Leu Asn
                485                 490                 495

Gly Leu Thr Leu Lys Met Val Asp Asp Gln Thr Leu Pro Pro Leu Met
            500                 505                 510

Glu Lys Pro Leu Arg Pro Gly Ser Ser Leu Gly Leu Pro Ala Phe Ser
        515                 520                 525

Tyr Ser Phe Phe Val Ile Arg Asn Ala Lys Val Ala Ala Cys Ile
    530                 535                 540

<210> SEQ ID NO 4
<211> LENGTH: 523
<212> TYPE: PRT
<213> ORGANISM: Gallus gallus

<400> SEQUENCE: 4

Met Leu Val Leu Leu Leu Val Leu Leu Ala Val Pro Pro Arg
1               5                   10                  15

Arg Thr Ala Glu Leu Gln Leu Gly Leu Arg Glu Pro Ile Gly Ala Val
                20                  25                  30

Ser Pro Ala Phe Leu Ser Leu Thr Leu Asp Ala Ser Leu Ala Arg Asp
            35                  40                  45

Pro Arg Phe Val Ala Leu Leu Arg His Pro Lys Leu His Thr Leu Ala
        50                  55                  60

Ser Gly Leu Ser Pro Gly Phe Leu Arg Phe Gly Gly Thr Ser Thr Asp
65                  70                  75                  80

Phe Leu Ile Phe Asn Pro Asn Lys Asp Ser Thr Trp Glu Glu Lys Val
                85                  90                  95

Leu Ser Glu Phe Gln Ala Lys Asp Val Cys Glu Ala Trp Pro Ser Phe
            100                 105                 110

Ala Val Val Pro Lys Leu Leu Leu Thr Gln Trp Pro Leu Gln Glu Lys
        115                 120                 125

Leu Leu Leu Ala Glu His Ser Trp Lys Lys His Lys Asn Thr Thr Ile
130                 135                 140

Thr Arg Ser Thr Leu Asp Ile Leu His Thr Phe Ala Ser Ser Ser Gly
145                 150                 155                 160

Phe Arg Leu Val Phe Gly Leu Asn Ala Leu Leu Arg Arg Ala Gly Leu
                165                 170                 175

Gln Trp Asp Ser Ser Asn Ala Lys Gln Leu Leu Gly Tyr Cys Ala Gln
            180                 185                 190

Arg Ser Tyr Asn Ile Ser Trp Glu Leu Gly Asn Glu Pro Asn Ser Phe
        195                 200                 205

Arg Lys Lys Ser Gly Ile Cys Ile Asp Gly Phe Gln Leu Gly Arg Asp
    210                 215                 220

Phe Val His Leu Arg Gln Leu Leu Ser Gln His Pro Leu Tyr Arg His
225                 230                 235                 240

Ala Glu Leu Tyr Gly Leu Asp Val Gly Gln Pro Arg Lys His Thr Gln
                245                 250                 255

His Leu Leu Arg Ser Phe Met Lys Ser Gly Gly Lys Ala Ile Asp Ser
            260                 265                 270

Val Thr Trp His His Tyr Tyr Val Asn Gly Arg Ser Ala Thr Arg Glu
        275                 280                 285
```

Asp Phe Leu Ser Pro Glu Val Leu Asp Ser Phe Ala Thr Ala Ile His
    290                 295                 300

Asp Val Leu Gly Ile Val Glu Ala Thr Val Pro Gly Lys Lys Val Trp
305                 310                 315                 320

Leu Gly Glu Thr Gly Ser Ala Tyr Gly Gly Ala Pro Gln Leu Ser
                325                 330                 335

Asn Thr Tyr Val Ala Gly Phe Met Trp Leu Asp Lys Leu Gly Leu Ala
            340                 345                 350

Ala Arg Arg Gly Ile Asp Val Val Met Arg Gln Val Ser Phe Gly Ala
        355                 360                 365

Gly Ser Tyr His Leu Val Asp Ala Gly Phe Lys Pro Leu Pro Asp Tyr
    370                 375                 380

Trp Leu Ser Leu Leu Tyr Lys Arg Leu Val Gly Thr Arg Val Leu Gln
385                 390                 395                 400

Ala Ser Val Glu Gln Ala Asp Ala Arg Arg Pro Arg Val Tyr Leu His
                405                 410                 415

Cys Thr Asn Pro Arg His Pro Lys Tyr Arg Glu Gly Asp Val Thr Leu
            420                 425                 430

Phe Ala Leu Asn Leu Ser Asn Val Thr Gln Ser Leu Gln Leu Pro Lys
        435                 440                 445

Gln Leu Trp Ser Lys Ser Val Asp Gln Tyr Leu Leu Leu Pro His Gly
    450                 455                 460

Lys Asp Ser Ile Leu Ser Arg Glu Val Gln Leu Asn Gly Arg Leu Leu
465                 470                 475                 480

Gln Met Val Asp Asp Glu Thr Leu Pro Ala Leu His Glu Met Ala Leu
                485                 490                 495

Ala Pro Gly Ser Thr Leu Gly Leu Pro Ala Phe Ser Tyr Gly Phe Tyr
            500                 505                 510

Val Ile Arg Asn Ala Lys Ala Ile Ala Cys Ile
        515                 520

<210> SEQ ID NO 5
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 5
tttttttttt ttttt                                                 15

<210> SEQ ID NO 6
<211> LENGTH: 36
<212> TYPE: DNA
<213> ORGANISM: Artificial sequence
<220> FEATURE:
<223> OTHER INFORMATION: synthetic polynucleotide
<221> NAME/KEY: misc_feature
<222> LOCATION: (24)..(25)
<223> OTHER INFORMATION: modified base : Inosine
<221> NAME/KEY: misc_feature
<222> LOCATION: (29)..(30)
<223> OTHER INFORMATION: modified base : Inosine
<221> NAME/KEY: misc_feature
<222> LOCATION: (34)..(35)
<223> OTHER INFORMATION: modified base : Inosine

<400> SEQUENCE: 6
ggccacgcgt cgactagtac gggnngggnn gggnng                          36

<210> SEQ ID NO 7
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 7
gactcctcaa gcattccctc ag                                         22

<210> SEQ ID NO 8
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 8
ggccacgcgt cgactagtac g                                          21

<210> SEQ ID NO 9
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 9
agccctgtta ctctgcgtgc tc                                         22

<210> SEQ ID NO 10
<211> LENGTH: 1605
<212> TYPE: DNA
<213> ORGANISM: Gallus gallus

<400> SEQUENCE: 10
aaggtgagaa ggaggaggaa ggatgctggt gctgctgctg ctcgtgctgc tgctcgctgt      60
gccgccgagg cggacggcag agctgcagct ggggctgcgg gaacccatcg ggcggtaag      120
cccagccttc ctctctctta cactggacgc cagcttggcc cgtgacccgc gctttgttgc     180
cctgctcaga cacccaagc tgcacactct ggccagtggg ctctccccag gcttcctcag     240
gtttggtggc accagtacag atttcctgat cttcaatccc aacaaagatt caacttggga     300
agagaaagtc ttgtcggaat tcaggccaa ggatgtgtgt gaagcgtggc ccagctttgc      360
tgtggttcca agctgctgc tcacccagtg gcccctccag gagaaactgc tcctcgctga     420
acattcctgg aaaaagcaca aaaacaccac cattacaagg agcacgctgg acatcctcca     480
cacgttcgcc agcagctcag gcttccgcct ggtgtttggg ctgaacgcac tgctgcgcag     540
ggctggcctg cagtgggaca gctccaacgc caagcagctg ctgggctact gtgcacagcg     600
cagctacaac atctcctggg agctgggtaa tgagcccaac agcttcagga agaagtcggg     660
catctgcatc gatggcttcc agttgggacg tgatttcgtc cacctgcggc agctcctgag     720
ccagcacccc ctgtaccgac acgctgagct gtacggcctc gacgtggggc agccccgcaa     780
gcacacccag cacctgctca agagcttcat gaaatctgga gggaaggcga ttgactcggt     840
cacctggcac cactactatg tgaatggccg aagtgcaacg agggaggatt tcctgagccc     900
tgaagtgctg gactccttg ccactgccat acacgatgtc ctgggatcg tggaagcaac       960
ggtgcccggc aagaaggtat ggctgggtga ccggctcg gctacggcg ggggggcccc        1020
ccagctctcc aacaccctatg tggccggctt catgtggctg acaagctggg ggttggcggc    1080

-continued

```
tcggcgtggc attgatgtgg tgatgaggca ggtctccttt ggtgctggca gctatcacct      1140
ggtggatgcc ggcttcaagc ccttgccgga ctactggctg tcactgctat acaagaggct      1200
ggtgggcacc cgggtactac aggccagcgt ggagcaagcg gatgcgcggc gcccgcgggt      1260
ctacctgcac tgcaccaacc cccggcaccc caaataccgg gaaggggatg tgacactgtt      1320
tgccttgaac ctctccaacg tgacccagag cttgcagctg cctaagcagt tgtggagtaa      1380
gagtgtggat cagtacctgc tgctgcccca cggcaaggac agcatcctgt ccagagaggt      1440
gcagctgaat ggccgcctac tgcagatggt ggacgatgag acactccccg cgctgcacga      1500
gatggccctt gccctggca gcacgctcgg cctgccagcc ttctcttacg gtttctacgt       1560
gatcaggaac gctaaggcta ttgcttgcat ttgagcacgc agagt                      1605
```

<210> SEQ ID NO 11
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 11

```
cggggtaccc gatgctggtg ct                                                 22
```

<210> SEQ ID NO 12
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 12

```
aggtccacga cgtcctgtgc cgtccgcctc g                                       31
```

<210> SEQ ID NO 13
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 13

```
cgaggcggac ggcacaggac gtcgtggacc t                                       31
```

<210> SEQ ID NO 14
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 14

```
ccacatcagg agggatggat cc                                                 22
```

<210> SEQ ID NO 15
<211> LENGTH: 1584
<212> TYPE: DNA
<213> ORGANISM: Artificial sequence
<220> FEATURE:
<223> OTHER INFORMATION: Chicken signal peptide/Human heparanase chimera
      coding sequence

<400> SEQUENCE: 15

```
atgctggtgc tgctgctgct cgtgctgctg ctcgctgtgc cgccgaggcg gacggcacag       60
```

```
gacgtcgtgg acctggactt cttcacccag gagccgctgc acctggtgag cccctcgttc    120
ctgtccgtca ccattgacgc caacctggcc acggacccgc ggttcctcat cctcctgggt    180
tctccaaagc ttcgtacctt ggccagaggc ttgtctcctg cgtacctgag gtttggtggc    240
accaagacag acttcctaat tttcgatccc aagaaggaat caacctttga agagagaagt    300
tactggcaat ctcaagtcaa ccaggatatt tgcaaatatg gatccatccc tcctgatgtg    360
gaggagaagt tacggttgga atggccctac caggagcaat tgctactccg agaacactac    420
cagaaaaagt tcaagaacag cacctactca agaagctctg tagatgtgct atacactttt    480
gcaaactgct caggactgga cttgatcttt ggcctaaatg cgttattaag aacagcagat    540
ttgcagtgga acagttctaa tgctcagttg ctcctggact actgctcttc caaggggtat    600
aacatttctt gggaactagg caatgaacct aacagtttcc ttaagaaggc tgatattttc    660
atcaatgggt cgcagttagg agaagatttt attcaattgc ataaacttct aagaaagtcc    720
accttcaaaa atgcaaaact ctatggtcct gatgttggtc agcctcgaag aaagacggct    780
aagatgctga gagcttcct gaaggctggt ggagaagtga ttgattcagt tacatggcat    840
cactactatt tgaatggacg gactgctacc agggaagatt ttctaaaccc tgatgtattg    900
gacattttta tttcatctgt gcaaaaagtt ttccaggtgg ttgagagcac caggcctggc    960
aagaaggtct ggttaggaga aacaagctct gcatatggag gcggagcgcc cttgctatcc   1020
gacacctttg cagctggctt tatgtggctg gataaattgg gcctgtcagc ccgaatggga   1080
atagaagtgg tgatgaggca gtattctttt ggagcaggaa actaccattt agtggatgaa   1140
aacttcgatc ctttacctga ttattggcta tctcttctgt tcaagaaatt ggtgggcacc   1200
aaggtgttaa tggcaagcgt gcaaggttca agagaaggaa agcttcgagt ataccttcat   1260
tgcacaaaca ctgacaatcc aaggtataaa gaaggagatt taactctgta tgccataaac   1320
ctccataacg tcaccaagta cttgcggtta ccctatcctt tttctaacaa gcaagtggat   1380
aaataccttc taagaccttt gggacctcat ggattacttt ccaaatctgt ccaactcaat   1440
ggtctaactc taaagatggt ggatgatcaa accttgccac ctttaatgga aaaacctctc   1500
cggccaggaa gttcactggg cttgccagct ttctcatata gttttttttgt gataagaaat   1560 gccaaagttg ctgcttgcat ctga                                          1584
```

<210> SEQ ID NO 16
<211> LENGTH: 527
<212> TYPE: PRT
<213> ORGANISM: Artificial sequence
<220> FEATURE:
<223> OTHER INFORMATION: Chicken signal peptide/Human heparanase chimera
      protein sequence

<400> SEQUENCE: 16

```
Met Leu Val Leu Leu Leu Val Leu Leu Leu Ala Val Pro Pro Arg
1               5                   10                  15

Arg Thr Ala Gln Asp Val Val Asp Leu Asp Phe Phe Thr Gln Glu Pro
            20                  25                  30

Leu His Leu Val Ser Pro Ser Phe Leu Ser Val Thr Ile Asp Ala Asn
        35                  40                  45

Leu Ala Thr Asp Pro Arg Phe Leu Ile Leu Leu Gly Ser Pro Lys Leu
    50                  55                  60

Arg Thr Leu Ala Arg Gly Leu Ser Pro Ala Tyr Leu Arg Phe Gly Gly
65                  70                  75                  80
```

-continued

Thr Lys Thr Asp Phe Leu Ile Phe Asp Pro Lys Lys Glu Ser Thr Phe
            85                  90                  95

Glu Glu Arg Ser Tyr Trp Gln Ser Gln Val Asn Gln Asp Ile Cys Lys
            100                 105                 110

Tyr Gly Ser Ile Pro Pro Asp Val Glu Glu Lys Leu Arg Leu Glu Trp
            115                 120                 125

Pro Tyr Gln Glu Gln Leu Leu Leu Arg Glu His Tyr Gln Lys Lys Phe
    130                 135                 140

Lys Asn Ser Thr Tyr Ser Arg Ser Ser Val Asp Val Leu Tyr Thr Phe
145                 150                 155                 160

Ala Asn Cys Ser Gly Leu Asp Leu Ile Phe Gly Leu Asn Ala Leu Leu
                165                 170                 175

Arg Thr Ala Asp Leu Gln Trp Asn Ser Ser Asn Ala Gln Leu Leu Leu
            180                 185                 190

Asp Tyr Cys Ser Ser Lys Gly Tyr Asn Ile Ser Trp Glu Leu Gly Asn
            195                 200                 205

Glu Pro Asn Ser Phe Leu Lys Lys Ala Asp Ile Phe Ile Asn Gly Ser
    210                 215                 220

Gln Leu Gly Glu Asp Phe Ile Gln Leu His Lys Leu Leu Arg Lys Ser
225                 230                 235                 240

Thr Phe Lys Asn Ala Lys Leu Tyr Gly Pro Asp Val Gly Gln Pro Arg
                245                 250                 255

Arg Lys Thr Ala Lys Met Leu Lys Ser Phe Leu Lys Ala Gly Gly Glu
            260                 265                 270

Val Ile Asp Ser Val Thr Trp His His Tyr Tyr Leu Asn Gly Arg Thr
            275                 280                 285

Ala Thr Arg Glu Asp Phe Leu Asn Pro Asp Val Leu Asp Ile Phe Ile
    290                 295                 300

Ser Ser Val Gln Lys Val Phe Gln Val Val Glu Ser Thr Arg Pro Gly
305                 310                 315                 320

Lys Lys Val Trp Leu Gly Glu Thr Ser Ser Ala Tyr Gly Gly Gly Ala
                325                 330                 335

Pro Leu Leu Ser Asp Thr Phe Ala Ala Gly Phe Met Trp Leu Asp Lys
            340                 345                 350

Leu Gly Leu Ser Ala Arg Met Gly Ile Glu Val Val Met Arg Gln Val
            355                 360                 365

Phe Phe Gly Ala Gly Asn Tyr His Leu Val Asp Glu Asn Phe Asp Pro
    370                 375                 380

Leu Pro Asp Tyr Trp Leu Ser Leu Leu Phe Lys Lys Leu Val Gly Thr
385                 390                 395                 400

Lys Val Leu Met Ala Ser Val Gln Gly Ser Lys Arg Arg Lys Leu Arg
                405                 410                 415

Val Tyr Leu His Cys Thr Asn Thr Asp Asn Pro Arg Tyr Lys Glu Gly
            420                 425                 430

Asp Leu Thr Leu Tyr Ala Ile Asn Leu His Asn Val Thr Lys Tyr Leu
            435                 440                 445

Arg Leu Pro Tyr Pro Phe Ser Asn Lys Gln Val Asp Lys Tyr Leu Leu
    450                 455                 460

Arg Pro Leu Gly Pro His Gly Leu Leu Ser Lys Ser Val Gln Leu Asn
465                 470                 475                 480

Gly Leu Thr Leu Lys Met Val Asp Asp Gln Thr Leu Pro Pro Leu Met
                485                 490                 495

Glu Lys Pro Leu Arg Pro Gly Ser Ser Leu Gly Leu Pro Ala Phe Ser

```
                   500               505               510
Tyr Ser Phe Phe Val Ile Arg Asn Ala Lys Val Ala Ala Cys Ile
            515               520               525
```

AVIAN AND REPTILE DERIVED POLYNUCLEOTIDE ENCODING A POLYPEPTIDE HAVING HEPARANASE ACTIVITY

This is a continuation-in-part of U.S. patent application Ser. No. 09/666,390, filed Sep. 20, 2000.

FIELD AND BACKGROUND OF THE INVENTION

The present invention relates to an avian and reptile derived polynucleotide encoding a polypeptide having heparanase catalytic activity. The present invention further relates to the use of the signal peptide of avian and/or reptile heparanase for expression of membrane associated and/or secreted proteins in heterologous expression systems.

Glycosaminoglycans (GAGs)

GAGs are polymers of repeated disaccharide units consisting of uronic acid and a hexosamine. Biosynthesis of GAGs except hyaluronic acid is initiated from a core protein. Proteoglycans may contain several GAG side chains from similar or different families. GAGs are synthesized as homopolymers which may subsequently be modified by N-deacetylation and N-sulfation, followed by C5-epimerization of glucuronic acid to iduronic acid and O-sulfation. The chemical composition of GAGs from various tissues varies highly.

The natural metabolism of GAGs in animals is carried out by hydrolysis. Generally, the GAGs are degraded in a two step procedure. First the proteoglycans are internalized in endosomes, where initial depolymerization of the GAG chain takes place. This step is mainly hydrolytic and yields oligosaccharides. Further degradation is carried out following fusion with lysosome, where desulfation and exolytic depolymerization to monosaccharides take place (42).

The only GAG degrading endolytic enzymes characterized so far in animals are the hyaluronidases. The hyaluronidases are a family of 1–4 endoglucosaminidases that depolymerize hyaluronic acid and chondroitin sulfate. The cDNAs encoding sperm associated PH-20 (Hyal3), and the lysosomal hyaluronidases Hyal 1 and Hyal 2 were cloned and published (27). These enzymes share an overall homology of 40% and have different tissue specificities, cellular localizations and pH optima for activity.

Exolytic hydrolases are better characterized, among which are β-glucoronidase, α-L-iduronidase, and β-N-acetylglucosaminidase. In addition to hydrolysis of the glycosidic bond of the polysaccharide chain, GAG degradation involves desulfation, which is catalyzed by several lysosomal sulfatases such as N-acetylgalactosamine-4-sulfatase, iduronate-2-sulfatase and heparin sulfamidase. Deficiency in any of lysosomal GAG degrading enzymes results in a lysosomal storage disease, mucopolysaccharidosis.

Glycosyl Hydrolases

Glycosyl hydrolases are a widespread group of enzymes that hydrolyze the o-glycosidic bond between two or more carbohydrates or between a carbohydrate and a noncarbohydrate moiety. The enzymatic hydrolysis of glycosidic bond occurs by using major one or two mechanisms leading to overall retention or inversion of the anomeric configuration. In both mechanisms, catalysis involves two residues: a proton donor and a nucleophile. Glycosyl hydrolyses have been classified into 58 families based on amino acid similarities. The glycosyl hydrolyses from families 1, 2, 5, 10, 17, 30, 35, 39 and 42 act on a large variety of substrates, however, they all hydrolyze the glycosidic bond in a general acid catalysis mechanism, with retention of the anomeric configuration. The mechanism involves two glutamic acid residues, which are the proton donor and the nucleophile, with an aspargine which always precedes the proton donor. Analyses of a set of known 3D structures from this group of enzymes revealed that their catalytic domains, despite the low level of sequence identity, adopt a similar $(\alpha/\beta)$ 8 fold with the proton donor and the nucleophile located at the C-terminal ends of strands $\beta 4$ and $\beta 7$, respectively. Mutations in the functional conserved amino acids of lysosomal glycosyl hydrolases were identified in lysosomal storage diseases.

Lysosomal glycosyl hydrolases including β-glucuronidase, β-manosidase, β-glucocerebrosidase, β-galactosidase and α-L-iduronidase, are all exo-glycosyl hydrolases, belong to the GH-A clan and share a similar catalytic site. However, many endo-glucanases from various organisms, such as bacterial and fungal xylenases and cellulases share this catalytic domain (1).

Heparan Sulfate Proteoglycans (HSPGs)

HSPGs are ubiquitous macromolecules associated with the cell surface and extracellular matrix (ECM) of a wide range of cells of vertebrate and invertebrate tissues (3–7). The basic HSPG structure consists of a protein core to which several linear heparan sulfate chains are covalently attached. The polysaccharide chains are typically composed of repeating hexuronic and D-glucosamine disaccharide units that are substituted to a varying extent with N- and O-linked sulfate moieties and N-linked acetyl groups (3–7). Studies on the involvement of ECM molecules in cell attachment, growth and differentiation revealed a central role of HSPGs in embryonic morphogenesis, angiogenesis, metastasis, neurite outgrowth and tissue repair (3–7). The heparan sulfate (HS) chains, which are unique in their ability to bind a multitude of proteins, ensure that a wide variety of effector molecules cling to the cell surface (6–8). HSPGs are also prominent components of blood vessels (5). In large vessels they are concentrated mostly in the intima and inner media, whereas in capillaries they are found mainly in the subendothelial basement membrane where they support proliferating and migrating endothelial cells and stabilize the structure of the capillary wall. The ability of HSPGs to interact with ECM macromolecules such as collagen, laminin and fibronectin, and with different attachment sites on plasma membranes suggests a key role for this proteoglycan in the self-assembly and insolubility of ECM components, as well as in cell adhesion and locomotion. Cleavage of HS may therefore result in disassembly of the subendothelial ECM and hence may play a decisive role in extravasation of normal and malignant blood-borne cells (9–11). HS catabolism is observed in inflammation, wound repair, diabetes, and cancer metastasis, suggesting that enzymes, which degrade HS, play important roles in pathologic processes.

Heparanase

Heparanase is a glycosylated enzyme that is involved in the catabolism of certain glycosaminoglycans. It is an endoglucuronidase that cleaves heparan sulfate at specific intrachain sites (12–15). Interaction of T and B lymphocytes, platelets, granulocytes, macrophages and mast cells with the subendothelial extracellular matrix (ECM) is associated with degradation of heparan sulfate by heparanase activity (16). Placenta heparanase acts as an adhesion molecule or as a degradative enzyme depending on the pH of the microenvironment (17).

Heparanase is released from intracellular compartments (e.g., lysosomes, specific granules) in response to various activation signals (e.g., thrombin, calcium ionophores, immune complexes, antigens and mitogens), suggesting its regulated involvement in inflammation and cellular immunity responses (16).

It was also demonstrated that heparanase can be readily released from human neutrophils by 60 minutes incubation at 4° C. in the absence of added stimuli (18).

Gelatinase, another ECM degrading enzyme, which is found in tertiary granule s of human neutrophils with heparanase, is secreted from the neutrophils in response to phorbol 12-myristate 13-acetate (PMA) treatment (19–20).

In contrast, various tumor cells appear to express and secrete heparanase in a constitutive manner in correlation with their metastatic potential (21).

Degradation of heparan sulfate by heparanase results in the release of heparin-binding growth factors, enzymes and plasma proteins that are sequestered by heparan sulfate in basement membranes, extracellular matrices and cell surfaces (22–23).

Heparanase activity has been described in a number of cell types including cultured skin fibroblasts, human neutrophils, activated rat T-lymphocytes, normal and neoplastic murine B-lymphocytes, human monocytes and human umbilical vein endothelial cells, SK hepatoma cells, human placenta and human platelets.

A procedure for purification of natural heparanase was reported for SK hepatoma cells and human placenta (U.S. Pat. No. 5,362,641) and for human platelets derived enzymes (62).

Cloning and Expression of the Human Heparanase Gene

The human hpa cDNA, which encodes human heparanase, was cloned from human placenta. It contained an open reading frame, which encodes a polypeptide of 543 amino acids with a calculated molecular weight of 61,192 daltons (2). The cloning procedures are described in length in U.S. patent application Ser. Nos. 08/922,170, 09/109,386, and 09/258,892, the latter is a continuation-in-part of PCT/US98/17954, filed Aug. 31, 1998, all of which are incorporated herein by reference. An identical cDNA encoding human heparanase was isolated later on from hepatoma cell line SK-hep1 (54). From platelets (55, 57, PCT/US99/01489, PCT/AU98/00898) and from SV40 transformed fibroblasts (56, PCT/EP99/00777).

The genomic locus, which encodes heparanase, spans about 40 kb. It is composed of 12 exons separated by 11 introns and is localized on human chromosome 4.

The ability of the hpa gene product to catalyze degradation of heparan sulfate (HS) in vitro was examined by expressing the entire open reading frame of hpa in High five and Sf21 insect cells, and the mammalian human 293 embryonic kidney cell line expression systems. Extracts of infected or transfected cells were assayed for heparanase catalytic activity. For this purpose, cell lysates were incubated with sulfate labeled, ECM-derived HSPG (peak I), followed by gel filtration analysis (SEPHAROSE 6B™) of the reaction mixture. While the substrate alone consisted of high molecular weight material, incubation of the HSPG substrate with lysates of cells infected or transfected with hpa containing vectors resulted in a complete conversion of the high molecular weight substrate into low molecular weight labeled heparan sulfate degradation fragments (see, for example, U.S. patent application Ser. No. 09/071,618, which is incorporated herein by reference.

In other experiments, it was demonstrated that the heparanase enzyme expressed by cells infected with a pFhpa virus is capable of degrading HS complexed to other macromolecular constituents (e.g., fibronectin, laminin, collagen) present in a naturally produced intact ECM (see U.S. patent application Ser. No. 09/109,386, which is incorporated herein by reference), in a manner similar to that reported for highly metastatic tumor cells or activated cells of the immune system (7, 8).

In human primary fibroblasts transfected with the heparanase cDNA the enzyme was localized to the lysosomes.

Preferential Expression of the hpa Gene Human Breast and Hepatocellular Carcinomas Semi-quantitative RT-PCR was employed to evaluate the expression of the hpa gene by human breast carcinoma cell lines exhibiting different degrees of metastasis. A marked increase in hpa gene expression is observed which correlates to metastatic capacity of non-metastatic MCF-7 breast carcinoma, moderately metastatic MDA 231 and highly metastatic MDA 435 breast carcinoma cell lines. Significantly, the differential pattern of the hpa gene expression correlated with the pattern of heparanase activity.

Expression of the hpa gene in human breast carcinoma was demonstrated by in situ hybridization to archival paraffin embedded human breast tissue. Hybridization of the heparanase antisense riboprobe to invasive duct carcinoma tissue sections resulted in a massive positive staining localized specifically to the carcinoma cells. The hpa gene was also expressed in areas adjacent to the carcinoma showing fibrocystic changes. Normal breast tissue derived from reduction mammoplasty failed to express the hpa transcript. High expression of the hpa gene was also observed in tissue sections derived from human hepatocellular carcinoma specimens but not in normal adult liver tissue. Furthermore, tissue specimens derived from adenocarcinoma of the ovary, squamous cell carcinoma of the cervix and colon adenocarcinoma exhibited strong staining with the hpa RNA probe, as compared to a very low staining of the hpa mRNA in the respective non-malignant control tissues (2).

A preferential expression of heparanase in human tumors versus the corresponding normal tissues was also noted by immunohistochemical staining of paraffin embedded sections with monoclonal anti-heparanase antibodies. Positive cytoplasmic staining was found in neoplastic cells of the colon carcinoma and in dysplastic epithelial cells of a tubulovillous adenoma found in the same specimen while there was little or no staining of the normal looking colon epithelium located away from the carcinoma. Of particular significance was an intense immunostaining of colon adenocarcinoma cells that had metastasized into lymph nodes, lung and liver, as compared to the surrounding normal tissues (58).

Latent and Active Forms of the Heparanase Protein

The apparent molecular size of the recombinant enzyme produced in the baculovirus expression system was about 65 kDa. This heparanase polypeptide contains 6 potential N-glycosylation sites. Following deglycosylation by treatment with peptide N-glycosidase, the protein appeared as a 57 kDa band. This molecular weight corresponds to the deduced molecular mass (61,192 daltons) of the 543 amino acid polypeptide encoded by the full length hpa cDNA after cleavage of the predicted 3 kDa signal peptide. No further reduction in the apparent size of the N-deglycosylated protein was observed following concurrent O-glycosidase and neuraminidase treatment. Deglycosylation had no detectable effect on enzymatic activity.

Unlike the baculovirus enzyme, expression of the full length heparanase polypeptide in mammalian cells (e.g., 293 kidney cells, CHO) yielded a major protein of about 50 kDa and a minor about 65 kDa protein in cell lysates. Comparison of the enzymatic activity of the two forms, using a semi-quantitative gel filtration assay, revealed that the 50 kDa enzyme is at least 100-fold more active than the 65 kDa form, which activity may be attributed to minute contamination by the 50 kDa protein in the analyzed samples. A similar difference was observed when the specific activity of the recombinant 65 kDa baculovirus enzyme was compared to that of the 50 kDa heparanase preparations purified from human platelets, SK-hep-1 cells, or placenta. These results suggest that the 50 kDa protein is a mature processed form of a latent heparanase precursor. Amino terminal sequencing of the platelet heparanase indicated that cleavage occurs between amino acids $Gln^{157}$ and $Lys^{158}$. As indicated by the hydropathic plot of heparanase, this site is located within a hydrophillic peak, which is likely to be exposed and hence accessible to proteases.

Involvement of Heparanase in Tumor Cell Invasion and Metastasis

Circulating tumor cells arrested in the capillary beds often attach at or near the intercellular junctions between adjacent endothelial cells. Such attachment of the metastatic cells is followed by rupture of the junctions, retraction of the endothelial cell borders and migration through the breach in the endothelium toward the exposed underlying base membrane (BM) (24). Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase, etc.) are thought to be involved in degradation of BM (25). Among these enzymes is heparanase that cleaves HS at specific intrachain sites (16, 11). Expression of a HS degrading heparanase was found to correlate with the metastatic potential of mouse lymphoma (26), fibrosarcoma and melanoma (21) cells. Moreover, elevated levels of heparanase were detected in sera from metastatic tumor bearing animals and melanoma patients (21) and in tumor biopsies of cancer patients (12).

The inhibitory effect of various non-anticoagulant species of heparin on heparanase was examined in view of their potential use in preventing extravasation of blood-borne cells. Treatment of experimental animals with heparanase inhibitors markedly reduced (>90%) the incidence of lung metastases induced by B16 melanoma, Lewis lung carcinoma and mammary adenocarcinoma cells (12, 13, 28). Heparin fractions with high and low affinity to anti-thrombin III exhibited a comparable high anti-metastatic activity, indicating that the heparanase inhibiting activity of heparin, rather than its anticoagulant activity, plays a role in the anti-metastatic properties of the polysaccharide (12).

The direct role of heparanase in cancer metastasis was demonstrated by two experimental systems. The murine T-lymphoma cell line Eb has no detectable heparanase activity. Whether the introduction of the hpa gene into Eb cells would confer a metastatic behavior on these cells was investigated. To this purpose, Eb cells were transfected with a full length human hpa cDNA. Stable transfected cells showed high expression of the heparanase mRNA and enzyme activity. These hpa and mock transfected Eb cells were injected subcutaneously into DBA/2 mice and mice were tested for survival time and liver metastases. All mice (n=20) injected with mock transfected cells survived during the first 4 weeks of the experiment, while 50% mortality was observed in mice inoculated with Eb cells transfected with the hpa cDNA. The liver of mice inoculated with hpa transfected cells was infiltrated with numerous Eb lymphoma cells, as was evident both by macroscopic evaluation of the liver surface and microscopic examination of tissue sections. In contrast, metastatic lesions could not be detected by gross examination of the liver of mice inoculated with mock transfected control Eb cells. Few or no lymphoma cells were found to infiltrate the liver tissue. In a different model of tumor metastasis, transient transfection of the heparanase gene into low metastatic B16-F1 mouse melanoma cells followed by i.v. inoculation, resulted in a 4- to 5-fold increase in lung metastases.

Finally, heparanase externally adhered to B16-F1 melanoma cells increased the level of lung metastases in C57BL mice as compared to control mice (see U.S. patent application Ser. No. 09/260,037 which is incorporated herein by reference).

Possible Involvement of Heparanase in Tumor Angiogenesis

Fibroblast growth factors are a family of structurally related polypeptides characterized by high affinity to heparin (29). They are highly mitogenic for vascular endothelial cells and are among the most potent inducers of neovascularization (29–30). Basic fibroblast growth factor (bFGF) has been extracted from a subendothelial ECM produced in vitro (31) and from basement membranes of the cornea (32), suggesting that ECM may serve as a reservoir for bFGF. Immunohistochemical staining revealed the localization of bFGF in basement membranes of diverse tissues and blood vessels (23). Despite the ubiquitous presence of bFGF in normal tissues, endothelial cell proliferation in these tissues is usually very low, suggesting that bFGF is somehow sequestered from its site of action. Studies on the interaction of bFGF with ECM revealed that bFGF binds to HSPG in the ECM and can be released in an active form by HS degrading enzymes (33, 32, 34). It was demonstrated that heparanase activity expressed by platelets, mast cells, neutrophils, and lymphoma cells is involved in release of active bFGF from ECM and basement membranes (35), suggesting that heparanase activity may not only function in cell migration and invasion, but may also elicit an indirect neovascular response. These results suggest that the ECM HSPG provides a natural storage depot for bFGF and possibly other heparin-binding growth promoting factors (36, 37). Displacement of bFGF from its storage within basement membranes and ECM may therefore provide a novel mechanism for induction of neovascularization in normal and pathological situations.

Recent studies indicate that heparin and HS are involved in binding of bFGF to high affinity cell surface receptors and in bFGF cell signaling (38, 39). Moreover, the size of HS required for optimal effect was similar to that of HS fragments released by heparanase (40). Similar results were obtained with vascular endothelial cells growth factor (VEGF) (41), suggesting the operation of a dual receptor mechanism involving HS in cell interaction with heparin-binding growth factors. It is therefore proposed that restriction of endothelial cell growth factors in ECM prevents their systemic action on the vascular endothelium, thus maintaining a very low rate of endothelial cells turnover and vessel growth. On the other hand, release of bFGF from storage in ECM as a complex with HS fragment, may elicit localized endothelial cell proliferation and neovascularization in processes such as wound healing, inflammation and tumor development (36, 37).

The Involvement of Heparanase in other Physiological Processes and its Potential Therapeutic Applications Apart from its involvement in tumor cell metastasis, inflammation and autoimmunity, mammalian heparanase may be applied to modulate bioavailability of heparin-binding growth factors; cellular responses to heparin-binding growth factors (e.g., bFGF, VEGF) and cytokines (IL-8) (44, 41); cell interaction with plasma lipoproteins (49); cellular susceptibility to certain viral and some bacterial and protozoa infections (45–47); and disintegration of amyloid plaques (48).

Viral Infection

The presence of heparan sulfate on cell surfaces have been shown to be the principal requirement for the binding of Herpes Simplex (45) and Dengue (46) viruses to cells and for subsequent infection of the cells. Removal of the cell surface heparan sulfate by heparanase may therefore abolish virus infection. In fact, treatment of cells with bacterial heparitinase (degrading heparan sulfate) or heparinase (degrading heparan) reduced the binding of two related animal herpes viruses to cells and rendered the cells at least partially resistant to virus infection (45). There are some indications that the cell surface heparan sulfate is also involved in HIV infection (47).

Neurodegenerative Diseases

Heparan sulfate proteoglycans were identified in the prion protein amyloid plaques of Genstmann-Straussler Syndrome, Creutzfeldt-Jakob disease and Scrape (48). Heparanase may disintegrate these amyloid plaques, which are also thought to play a role in the pathogenesis of Alzheimer's disease.

Restenosis and Atherosclerosis

Proliferation of arterial smooth muscle cells (SMCs) in response to endothelial injury and accumulation of cholesterol rich lipoproteins are basic events in the pathogenesis of atherosclerosis and restenosis (50). Apart from its involvement in SMC proliferation as a low affinity receptor for heparin-binding growth factors, HS is also involved in lipoprotein binding, retention and uptake (51). It was demonstrated that HSPG and lipoprotein lipase participate in a novel catabolic pathway that may allow substantial cellular and interstitial accumulation of cholesterol rich lipoproteins (49). The latter pathway is expected to be highly atherogenic by promoting accumulation of apoB and apoE rich lipoproteins (e.g., LDL, VLDL, chylomicrons), independent of feed back inhibition by the cellular cholesterol content. Removal of SMC HS by heparanase is therefore expected to inhibit both SMC proliferation and lipid accumulation and thus may halt the progression of restenosis and atherosclerosis.

Pulmonary Diseases

The data obtained from the literature suggests a possible role for GAGs degrading enzymes, such as, but not limited to, heparanases, connective tissue activating peptide, heparinases, hyluronidases, sulfatases and chondroitinases, in reducing the viscosity of sinuses and airway secretions with associated implications on curtailing the rate of infection and inflammation. The sputum from CF patients contains at least 3% GAGs, thus contributing to its volume and viscous properties. We have shown that heparanase reduces the viscosity of sputum of Cystic fibrosis (CF) patients (U.S. patent application Ser. No. 09/046,475). Recombinant heparanase has been shown to reduce viscosity of sputum of CF patients (see, U.S. patent application Ser. No. 09/046, 475).

In summary, heparanase may thus prove useful for conditions such as wound healing, angiogenesis, restenosis, atherosclerosis, inflammation, neurodegenerative diseases and viral infections. Mammalian heparanase can be used to neutralize plasma heparin, as a potential replacement of protamine. Anti-heparanase antibodies may be applied for immunodetection and diagnosis of micrometastases, autoimmune lesions and renal failure in biopsy specimens, plasma samples, and body fluids.

There is thus a widely recognized need for, and it would be highly advantageous to have, additional molecules with glycosyl hydrolase activity, because such molecules may exhibit greater specific activity toward certain substrates or different substrate specificity than the known heparanase.

SUMMARY OF THE INVENTION

According to one aspect of the present invention there is provided an isolated nucleic acid comprising a genomic, complementary or composite polynucleotide sequence which (a) encodes a polypeptide which is at least 75% similar to SEQ ID NO:4 or a portion thereof as determined using the BESTFIT™ software of the Wisconsin sequence analysis package, utilizing the Smith and Waterman algorithm, where gap weight equals 8 and length weight equals 2, average match equals 2.912 and average mismatch equals −2.003; (b) is at least 65% identical to SEQ ID NO:10 or a portion thereof as determined using the BESTFIT™ software of the Wisconsin sequence analysis package, utilizing the Smith and Waterman algorithm, where gap weight equals 50, length weight equals 3, average match equals 10 and average mismatch equals −9; (c) is as set forth in SEQ ID NO:10 or a portion thereof; and/or (d) is hybridizable with SEQ ID NO:10 or a portion thereof under hybridization conditions of hybridization solution containing 10% dextrane sulfate, 1 M NaCl, 1% SDS and 5×10$^6$ cpm $^{32}$p labeled probe, at 65° C., with a final wash solution of 1×SSC and 0.1% SDS and final wash at 65° C.

According to a preferred embodiment of the present invention the polynucleotide encodes a polypeptide which has heparanase catalytic activity or which is cleavable by a protease so as to have the heparanase catalytic activity.

According to another aspect of the present invention there is provided a nucleic acid construct comprising any of the polynucleotides of the present invention in a sense or antisense orientation with respect to expression regulatory sequences of the construct.

According to yet another aspect of the present invention there is provided a cell transformed or transfected with polynucleotides or constructs of the present invention.

According to still another aspect of the present invention there is provided an oligonucleotide of at least 17 bases specifically hybridizable with the isolated nucleic acid described herein and which is not hybridizable with any mammalian heparanase cDNA.

According to an additional aspect of the present invention there is provided a pair of oligonucleotides each of at least 17 bases specifically hybridizable with the isolated nucleic acid described herein in an opposite orientation so as to direct exponential amplification of a portion thereof in a nucleic acid amplification reaction, and which are not hybridizable with any mammalian heparanase cDNA.

According to yet an additional aspect of the present invention there is provided a nucleic acid amplification product obtained using the pair of primers described herein.

According to yet a further aspect of the present invention there is provided a nucleic acid construct comprising a first polynucleotide encoding a signal peptide of avian or reptile heparanase and an in frame, second polynucleotide encoding a membrane targeted or secreted polypeptide.

According to still a further aspect of the present invention there is provided a nucleic acid construct comprising a first polynucleotide encoding an avian or reptile heparanase signal peptide, e.g., a peptide as set forth at positions 1 to 19 of SEQ ID NO:4, and an in frame, second polynucleotide encoding a membrane targeted or secreted polypeptide.

Preferably, the targeted or secreted polypeptide is human heparanase.

According to still an additional aspect of the present invention there is provided a method of expressing a protein of interest in a cell, the method comprising transforming the cell with a nucleic acid construct that comprises a first polynucleotide encoding a signal peptide of avian or reptile heparanase and an in frame, second polynucleotide encoding a membrane targeted or secreted polypeptide; and culturing the cell under suitable growth conditions.

As used herein the term "transforming" refers to any and all methods of permanent or transient introduction of foreign nucleic acids into cells, such as for example, plasmid transformation, phage infection, gene knock-in and the like.

According to yet an additional aspect of the present invention there is provided a recombinant protein comprising a polypeptide (a) which is at least 75% similar to SEQ ID NO:4 or a portion thereof as determined using the BESTFIT™ software of the Wisconsin sequence analysis package, utilizing the Smith and Waterman algorithm, where gap weight equals 8 and length weight equals 2, average match equals 2.912 and average mismatch equals −2.003; (b) encoded by a nucleic acid including a genomic, complementary or composite polynucleotide sequence being at least 65% identical to SEQ ID NO:10 or a portion thereof as determined using the BESTFIT™ software of the Wisconsin sequence analysis package, utilizing the Smith and Waterman algorithm, where gap weight equals 50, length weight equals 3, average match equals 10 and average mismatch equals −9; (c) encoded by a nucleic acid as set forth in SEQ ID NO:10 or a portion thereof; and/or encoded by a nucleic acid including a genomic, complementary or composite polynucleotide sequence being hybridizable with SEQ ID NO:10 or a portion thereof under hybridization conditions of hybridization solution containing 10% dextrane sulfate, 1 M NaCl, 1% SDS and 5×10$^6$ cpm $^{32}$p labeled probe, at 65° C., with a final wash solution of 1×SSC and 0.1% SDS and final wash at 65° C.

According to further features in preferred embodiments of the invention described below, the polypeptide has heparanase catalytic activity or the polypeptide is cleavable by a protease so as to have the heparanase catalytic activity.

According to a further aspect of the present invention there is provided a pharmaceutical composition comprising, as an active ingredient, the recombinant protein of described herein and a pharmaceutically acceptable carrier.

The present invention successfully addresses the shortcomings of the presently known configurations by providing novel polynucleotides which encode novel polypeptides having heparanase catalytic activity and which can be used to intervene with pathologies associated with impaired heparin-binding growth factors, cellular responses to heparin-binding growth factors and cytokines, cell interaction with plasma lipoproteins, cellular susceptibility to viral, protozoa and bacterial infections or disintegration of neurodegenerative plaques, all as is further delineated in the background section above.

BRIEF DESCRIPTION OF THE DRAWINGS

The file of this patent contains at least one drawings executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. The patent or application file contains at least one drawing executed in color. Copies of the patent or patent application publication with color drawing(s) will be provided by the U.S. Patent and Trademark Office upon request and payment of the necessary fee.

In the drawings:

FIG. 1a presents an alignment of the amino acid sequences of, mouse (SEQ ID NO:1), rat (SEQ ID NO:2), human (SEQ ID NO:3) and chicken (SEQ ID NO:4) heparanases. The amino acid sequences were determined by sequence analysis of the isolated cDNAs. The amino acids, which are identical in heparanases from the four organisms, are marked with an asterisk, conserved differences are marked by double or single dots. The putative two catalytic residues, the proton donor and the nucleophile are bolded. The signal peptide of human heparanase and the putative signal peptides of chicken mouse and rat heparanases are underlined. The cleavage site of the 50 kDa mature protein and the borders of the associated 8 kDa peptide are pointed by arrows. Multiple alignment was generated by ClustalW.

FIG. 1b presents the chicken heparanase coding sequence (SEQ ID NO:10) and its translation product (SEQ ID NO:4).

Figure 2:

FIG. 2 shows western analysis of heparanase secreted by Eb lymphoma cells transfected with chicken heparanase cDNA (Chk-hpa) and human heparanase cDNA (Hum-hpa). Heparanase was partially purified (SP-SEPHAROSE™) from serum free medium conditioned by Eb lymphoma cells transfected with Chk-hpa (lane 1), Hum-hpa (lane 2), or plasmid alone (lane 3). Protein samples were subjected to 10% SDS/PAGE and western blot analysis applying polyclonal rabbit anti-heparanase antibodies and ECL visualization. Protein bands correspond to the 58 kDa and 45 kDa forms of the chicken enzyme vs. the 65 kDa and 50 kDa latent and active human heparanase forms.

Figures 3A, 3B, 3C:
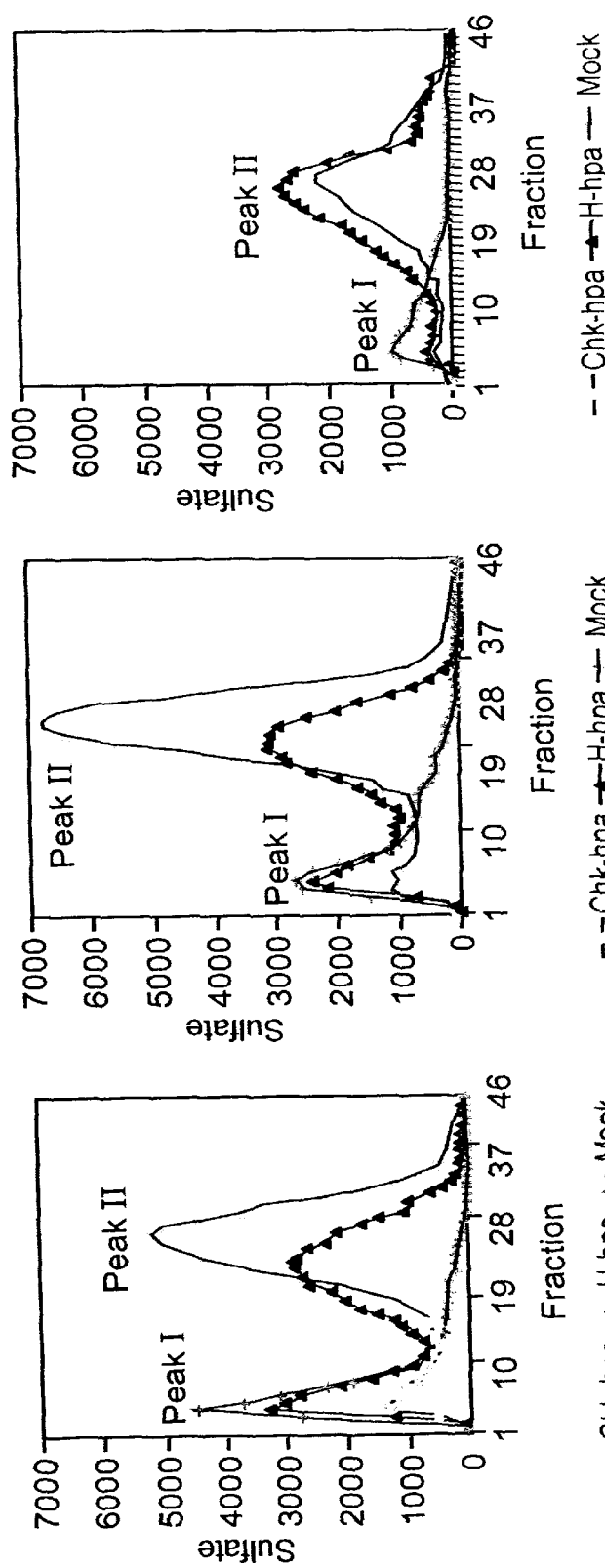

FIGS. 3a–c demonstrate heparanase activity in cell lysates, intact cells and medium conditioned by Eb cells transfected with chicken vs. human heparanases. Eb mouse lymphoma cells transfected with Chk-hpa (■), Hum-hpa (▼) and control vector (+) were maintained (24 h, 2×106 cells/ml) in serum free RPMI medium. Intact cells (3a), conditioned media (3b) and lysates (3c) of 2×10$^6$ cells were then tested for heparanase activity. For this purpose, 1 ml conditioned medium and 2×10$^6$ intact or lysed cells were incubated (24 h, 37° C., pH 6.2) in serum free medium with sulfate labeled ECM. Labeled degradation fragments released into the incubation medium were analyzed by gel filtration on SEPHAROSE 6B™. Nearly intact heparan sulfate proteoglycans elute next to $V_0$ (peak I, fractions 1–10) whereas heparan sulfate degradation products elute toward the $V_t$ of the column (peak II, fractions 15–35). A much higher heparanase activity was expressed by intact lymphoma cells (3a) and even more was secreted into the conditioned medium (3b) of cells transfected with the Chk-hpa as compared to cells transfected with the Hum-hpa. In contrast, there was no difference in heparanase activity found in the corresponding cell lysates (3c).

Figure 4:
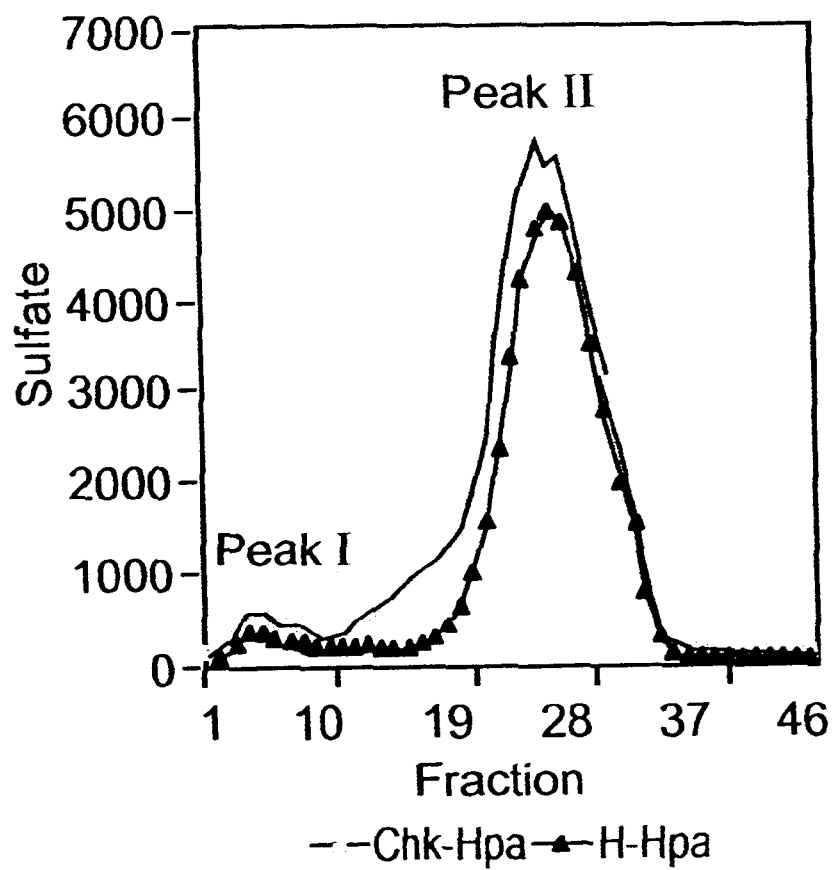

FIG. 4 presents a comparison of heparanase activities of partially purified chicken and human heparanases. Chicken and human heparanases were partially purified (SP SEPHAROSE™) from serum free medium conditioned by stable hpa transfected Eb lymphoma cells. Equal amounts (60 ng/ml) of partially purified chicken (■) and human (▼) heparanases were incubated (24 h, 37° C., pH 6.2) with sulfate labeled ECM. Labeled degradation fragments released into the incubation medium were analyzed by gel filtration on SEPHAROSE 6B™. Both enzymes exhibit a similar apparent specific activity, as indicated by an almost identical elution pattern of HS degradation products.

FIGS. 5a–d demonstrates the cellular localization of chicken (Chk-hpa) and chimeric (chimeric-hpa) heparanases vs. human (H-hpa) heparanase. C6 rat glioma cells were transfected with chicken (a), human (c), or chimeric (b) heparanase cDNAs. Pooled populations of stable transfected cells were subjected to indirect immunofluorescence staining with monoclonal anti-heparanase antibodies (mAb 130) followed by Cy-3 conjugated goat anti-mouse antibody, as described in the Examples section that follows. Mock transfected C6 glioma cells (d) were used as control and showed no staining. Chk-hpa (a) and chimeric-hpa (c) transfected cells exhibited intense staining associated mostly with the cell membrane (arrow), while cells transfected with H-hpa cDNA (b) displayed primarily a peri-nuclear granular staining (arrow). Bar=10 μM.

Figures 6, 7:
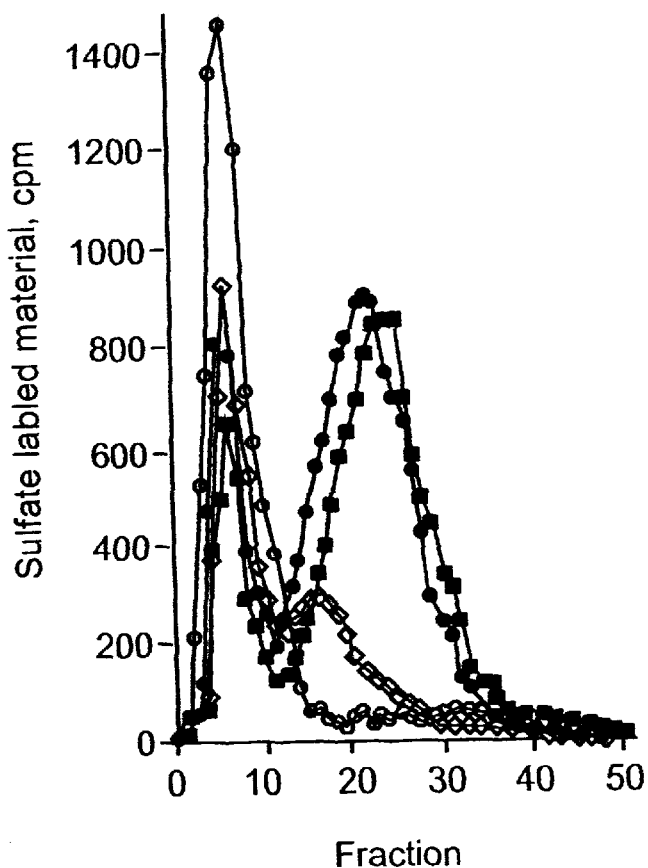

FIG. 6 presents the comparison between heparanases of human, chicken, mouse and rat. Percents of identity between the coding nucleotide sequences appear in the upper block. Percents of identity and similarity between the amino acid sequences appear in the lower right and lower left blocks, respectively. The nucleotide sequence was determined for each one of the four species and the amino acid sequence was deduced from the cDNA sequence.

FIG. 7 demonstrates the secretion of chicken and chimeric heparanases. Eb mouse lymphoma cells were stable transfected with Chk-hpa (■), H-hpa (?), or chimeric-hpa (?). Serum free medium conditioned by these cells was incubated (24 h, 37° C., pH 6.2) with sulfate labeled ECM and tested for heparanase activity. Mock transfected Eb lymphoma cells (○) were used as control.

DESCRIPTION OF THE PREFERRED EMBODIMENTS

The present invention is of an avian or reptile derived polynucleotide encoding a polypeptide having heparanase catalytic activity which can be used in a variety of medical applications. Specifically, the present invention can be used to intervene with pathologies associated with impaired heparin-binding growth factors, cellular responses to heparin-binding growth factors and cytokines, cell interaction with plasma lipoproteins, cellular susceptibility to viral, protozoa and bacterial infections or disintegration of neurodegenerative plaques, all as is further delineated in the background section above. The present invention is further of chimeric nucleic acids encoding, in frame, the signal peptide sequence of avian or reptile heparanase and a protein of interest, such as human heparanase.

The principles, operation and uses of the present invention may be better understood with reference to the drawings and accompanying descriptions.

Before explaining at least one embodiment of the invention in detail, it is to be understood that the invention is not limited in its application to the details set forth in the following description or illustrated in the examples. The invention is capable of other embodiments or of being practiced or carried out in various ways. Also, it is to be understood that the phraseology and terminology employed herein is for the purpose of description and should not be regarded as limiting.

In an attempt to isolate an avian heparanase encoding polynucleotide, cDNA libraries and reverse transcribed mRNA from avian tissue were screened via hybridization and polymerase chain reaction techniques using mammalian derived probes and oligonucleotides, yet with no successes even under the mildest hybridization conditions. The human heparanase amino acid sequence was thereafter used to screen EST databases for homology to a chicken unidentified mRNA sequences. Following extensive screening, a single related chicken EST was identified which shared 60.5% homology with the 276 bp at the 3' end of the human heparanase coding sequence. This sequence encoded a truncated open reading frame of 91 amino acids, 74% homologous to human heparanase, followed by 325 nucleotides 3' untranslated region (UTR). The heparanase homologous sequence was derived from chicken activated T cells cDNA, clone pat.pk0039.c8.f5', mRNA sequence, accession No. AI980994.

In order to isolate a full length clone and to test whether it is indeed heparanase, chicken kidney mRNA was subjected to 5' RACE (rapid amplification of cDNA ends). The gene specific PCR primers were designed according to the EST described above. A DNA fragment of approximately 1,600 bp was obtained, partially overlapping with the identified 3' encoding EST clone. The entire cDNA cloned, in pGEM-T EASY VECTOR™, was designated Chk-hpa. The complete cDNA (Chk-hpa) is 1,609 bp long (SEQ ID NO:10), and it contains an open reading frame that encodes a polypeptide of 523 amino acids (SEQ ID NO:4) with a calculated molecular weight of 58,842 Daltons. Analysis of the amino acid sequence and of the hydropathic profile of the protein indicates a hydrophobic amino acid tail at the N-terminus. A signal peptide is predicted to span the N-terminal 19 amino acids.

The overall homology between the chicken and the human heparanase coding sequences is 62%. The similarity between the chicken and the human heparanases is 69% (of which 61% amino acid sequence identity). The heparanase is synthesized as a latent, 65 kDa precursor and is then processed to an active mature 50 kDa form. Based on the homology to human heparanase the chicken heparanase is cleaved between Trp$^{136}$ and Lys$^{137}$. According to Fairbank et al. the precursor is cleaved at three sites to form a heterodimer of a 50 kDa polypeptide (the mature form) that is associated with a 8 kDa peptide. The putative chicken 8 kDa peptide spans amino acids $Glu^{10}$ to $Glu^{94}$. The mature heparanases of various organisms share high homology while the pro-peptides are relatively diverse.

Structure prediction of human heparanase suggests a $(\alpha/\beta)8$ Tim barrel fold typical of family 10 glycosyl hydrolases. According to this prediction the active site involves two glutamic acid residues, which are the proton donor and the nucleophile, with an aspargine always preceding the proton donor. The proton donor in human heparanase is $Glu^{225}$ and the nucleophile is $Glu^{343}$. The conservation of the amino acid sequence flanking these residues supports the identification of the active site. Based on the homology the proton donor of chicken heparanase is $Glu^{204}$ and the nucleophile is $Glu^{323}$.

Chicken heparanase is slightly more similar to human heparanase than to mouse and rat heparanases. As expected, the homology among mammals is far higher than that of mammals with chicken.

The ability of the Chk-Hpa product to catalyze degradation of heparan sulfate (HS) in vitro was determined by expressing the entire open reading frame of Chk-hpa in mammalian cells lacking heparanase activity. Expression of heparanase in the transfected cells was confirmed by RT-PCR. Chicken heparanase transcript was detected only in Chk-hpa transfected cells.

Heparanase activity was assayed in cells transfected with Chk-hpa as compared to mock transfected cells. High activity was observed in intact cells, conditioned media and cell lysates of Chk-hpa transfectants while no activity was observed in the mock transfected cells.

The heparan sulfate degradation activity of Eb cells transfected with Chk-hpa cDNA was compared with that of Eb cells transfected with human hpa (Hum-hpa). The activity of chicken heparanase was higher than that of human heparanase in intact cells and in conditioned media, however, in cell extracts the activity of the two enzymes was similar. This suggests that the chicken heparanase is unexpectedly preferentially secreted as is compared to the mammalian enzyme.

In order to compare the activity of the chicken and human heparanases, the enzymes were partially purified from conditioned media of Chk-hpa and Hum-hpa transfected cells. Western blot analysis of the partially purified chicken heparanase showed a major protein of 58 kDa, which corresponds to the heparanase precursor and a minor protein of 45 kDa, which corresponds to the mature form. The human heparanase fraction contained the equivalent human 65 kDa heparanase precursor and 50 kDa mature forms. The difference in molecular weight between chicken and human heparanases is mainly due to a different glycosylation pattern.

Activity of the two enzymes was compared using equal amounts of the partially purified enzymes in a semi-quantitative assay. The specific activity of chicken and human heparanases was found to be similar.

Cells transfected with Chk-hpa exhibited intense staining associated with the cell membrane while only a weak signal was observed in the cytoplasm. In contrast, in cells transfected with Hum-hpa heparanase is localized to peri-nuclear vesicles. A similar pattern was observed in transiently transfected human primary fibroblasts, where chicken heparanase was associated with cell membrane while human heparanase was localized to peri-nuclear vesicles, which were identified as lysosomes. The signal peptides of the chicken and human heparanases share no significant homology. It appears that the signal peptide of chicken heparanase unexpectedly targets the enzyme to the cell surface of mammalian cells while the signal peptide of human heparanase targets the enzyme to lysosomes. Indeed, replacing the signal peptide of human heparanase with that of chicken heparanase resulted in improved secretion and membrane localization of the human heparanase.

Thus, according to one aspect of the present invention there is provided an isolated nucleic acid comprising a genomic, complementary or composite polynucleotide sequence which (a) encodes a polypeptide which is at least 75% similar to SEQ ID NO:4 or a portion thereof as determined using the BESTFIT™ software of the Wisconsin sequence analysis package, utilizing the Smith and Waterman algorithm, where gap weight equals 8 and length weight equals 2, average match equals 2.912 and average mismatch equals −2.003; (b) is at least 65% identical to SEQ ID NO:10 or a portion thereof as determined using the BESTFIT™ software of the Wisconsin sequence analysis package, utilizing the Smith and Waterman algorithm, where gap weight equals 50, length weight equals 3, average match equals 10 and average mismatch equals −9; (c) is as set forth in SEQ ID NO:10 or a portion thereof; and/or (d) is hybridizable with SEQ iD NO:10 or a portion thereof under hybridization conditions of hybridization solution containing 10% dextrane sulfate, 1 M NaCl, 1% SDS and $5\times10^6$ cpm $^{32}p$ labeled probe, at 65° C., with a final wash solution of 1×SSC and 0.1% SDS and final wash at 65° C. Under these hybridization conditions the chicken heparanase cDNA fails to hybridize with any mammalian heparanase.

The phrase "composite polynucleotide sequence" refers to a sequence which includes exonal sequences required to encode the polypeptide having heparanase activity, as well as any number of intronal sequences. The intronal sequences can be of any source and typically will include conserved splicing signal sequences. Such intronal sequences may further include cis acting expression regulatory elements.

Thus, this aspect of the present invention encompasses (i) polynucleotides as set forth in SEQ ID NO:10; (ii) fragments thereof; (iii) sequences hybridizable therewith; (iv) sequences homologous thereto, such as reptile derived sequences; (v) sequences encoding similar polypeptides with different codon usage; (vi) altered sequences characterized by mutations, such as deletion, insertion or substitution of one or more nucleotides, either naturally occurring or man induced, either randomly or in a targeted fashion.

It will be appreciated in this respect that avian and reptiles are evolutionary closely related. As such, using the polynucleotides described herein, one of ordinary skills in the art, would be motivated and readily capable of screening a reptile cDNA library or use other methods routinely employed to isolate related genes from closely related species, to thereby clone full length cDNAs or genomic DNAs from any avian or reptile.

The heparanase sequence described herein can be used to study the catalytic mechanism of heparanase. Carefully selected site directed mutagenesis can be employed to provide modified heparanase proteins having modified characteristics in terms of, for example, substrate specificity, sensitivity to inhibitors, etc.

According to a preferred embodiment of the present invention the polynucleotide encodes a polypeptide which has heparanase catalytic activity or which is cleavable by a protease so as to have the heparanase catalytic activity.

Removal of a 19 amino acid long signal peptide of chicken heparanase is demonstrated in the Examples section that follows.

The term "heparanase catalytic activity" or its equivalent term "heparanase activity" both refer to a mammalian endoglycosidase hydrolyzing activity which is specific for heparin or heparan sulfate proteoglycan substrates, as opposed to the activity of bacterial enzymes (heparinase I, II and III) which degrade heparin or heparan sulfate by means of β-elimination (37).

According to another aspect of the present invention there is provided a nucleic acid construct comprising any of the polynucleotides of the present invention in a sense or antisense orientation with respect to expression regulatory sequences of the construct.

According to a preferred embodiment the nucleic acid construct according to this aspect of the present invention includes a promoter for regulating the expression of the isolated nucleic acid in a sense or antisense orientation. Such promoters are known to be cis-acting sequence elements required for transcription as they serve to bind DNA dependent RNA polymerase which transcribes sequences present downstream thereof. Such down stream sequences can be in either one of two possible orientations to result in the transcription of sense RNA which is translatable by the ribozyme machinery or antisense RNA which typically does not contain translatable sequences, yet can duplex or triplex with endogenous sequences, either mRNA or chromosomal DNA and hamper gene expression, all as further detailed hereinunder.

While the isolated nucleic acid described herein is an essential element of the invention, it is modular and can be used in different contexts. The promoter of choice that is used in conjunction with this invention is of secondary importance, and will comprise any suitable promoter. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest. These elements may be selected from transcriptional regulators that activate the transcription of genes essential for the survival of these cells in conditions of stress or starvation, including the heat shock proteins.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in *E. coli* (wherein the construct comprises an appropriate selectable marker and origin of replication) and be compatible for propagation in cells, or integration in the genome, of an organism of choice. The construct according to this aspect of the present invention can be, for example, a plasmid, a bacmid, a phagemid, a cosmid, a phage, a virus or an artificial chromosome.

The polynucleotide encoding heparanase can be permanently or transiently present in the cell. In other words, genetically modified cells obtained following stable or transient transfection, transformation or transduction are all within the scope of the present invention. The polynucleotide can be present in the cell in low copy (say 1–5 copies) or high copy number (say 5–50 copies or more). It may be integrated in one or more chromosomes at any location or be present as an extrachromosomal material.

Alternatively, the nucleic acid construct according to this aspect of the present invention further includes a positive and a negative selection markers and may therefore be employed for selecting for homologous recombination events, including, but not limited to, homologous recombination employed in knock-in and knock-out procedures. One ordinarily skilled in the art can readily design a knock-out or knock-in constructs including both positive and negative selection genes for efficiently selecting transfected embryonic stem cells that underwent a homologous recombination event with the construct. Such cells can be introduced into developing embryos to generate chimeras, the offspring thereof can be tested for carrying the knock-out or knock-in constructs. Additional detail can be found in Fukushige, S. and Ikeda, J. E.: Trapping of mammalian promoters by Cre-lox site-specific recombination. DNA Res 3 (1996) 73–80; Bedell, M. A., Jenkins, N. A. and Copeland, N. G.: Mouse models of human disease. Part I: Techniques and resources for genetic analysis in mice. Genes and Development 11 (1997) 1–11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751–62, which are incorporated herein by reference.

According to yet another aspect of the present invention there is provided a cell transformed or transfected with polynucleotides or constructs of the present invention. The cell according to this aspect of the present invention can be a eukaryote cell of a multicellular organism, such as, but not limited to, a mammalian, avian, reptile or insect cell, a eukaryote cell of a unicellular organism, such as yeast or a prokaryote cell, such as a bacteria cell, e.g., an *E. coli* cell. Methods of transforming and transfecting each of these cells are well known in the art. Such procedures are detailed in many experimental procedure text books such as "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds).

The present invention is further directed at providing a heparanase over-expression system which includes a cell overexpressing heparanase catalytic activity. The cell may be a genetically modified host cell transiently or stably transfected or transformed with any suitable vector which includes a polynucleotide sequence encoding a polypeptide having heparanase activity and a suitable promoter and enhancer sequences to direct over-expression of heparanase. However, the overexpressing cell may also be a product of an insertion (e.g., via homologous recombination) of a promoter and/or enhancer sequence downstream to the endogenous heparanase gene of the expressing cell, which will direct over-expression from the endogenous gene.

The term "over-expression" as used herein in the specification and claims below refers to a level of expression which is higher than a basal level of expression typically characterizing a given cell under otherwise identical conditions.

According to still another aspect of the present invention there is provided an oligonucleotide of at least 17, at least 18, at least 19, at least 20, at least 22, at least 25, at least 30 or at least 40 bases specifically hybridizable with the isolated nucleic acid described herein and which is not hybridizable with any mammalian heparanase cDNA.

Hybridization of shorter nucleic acids (below 200 bp in length, e.g. 17–40 bp in length) is effected by stringent, moderate or mild hybridization, wherein stringent hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1–1.5° C. below the $T_m$, final wash solution of 3 M TMACl, 0.01 M sodium phosphate (pH 6.8), 1 mM EDTA (pH 7.6), 0.5% SDS at 1–1.5° C. below the $T_m$; moderate hybridization is effected by a hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2–2.5° C. below the $T_m$, final wash solution of 3 M TMACl, 0.01 M sodium phosphate (pH 6.8), 1 mM EDTA (pH 7.6), 0.5% SDS at 1–1.5° C. below the $T_m$, final wash solution of 6×SSC, and final wash at 22° C.; whereas mild hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 37° C., final wash solution of 6×SSC and final wash at 22° C.

According to an additional aspect of the present invention there is provided a pair of oligonucleotides each of at least 17, at least 18, at least 19, at least 20, at least 22, at least 25, at least 30 or at least 40 bases specifically hybridizable with the isolated nucleic acid described herein in an opposite orientation so as to direct exponential amplification of a portion thereof in a nucleic acid amplification reaction, such as a polymerase chain reaction, and which are not hybridizable with any mammalian heparanase cDNA.

The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and zero ° C.

Consequently, according to yet an additional aspect of the present invention there is provided a nucleic acid amplification product obtained using the pair of primers described herein. Such a nucleic acid amplification product can be isolated by gel electrophoresis or any other size based separation technique. Alternatively, such a nucleic acid amplification product can be isolated by affinity separation, either stranded affinity or sequence affinity. In addition, once isolated, such a product can be further genetically manipulated by restriction, ligation and the like.

According to yet a further aspect of the present invention there is provided a nucleic acid construct comprising a first polynucleotide encoding a signal peptide of chicken and/or avian heparanase, such as the peptide set forth at positions 1 to 19 of SEQ ID NO:4, and an in frame, second polynucleotide encoding a membrane targeted or secreted polypeptide. The chimeric polypeptide resulting from the expression of the open reading frame of this construct will be preferentially directed to the cell membrane or secreted outside the cell, depending on the nature of the polypeptide. Any polypeptide can be fused to the signal peptide of the invention, including, but not limited to, any enzyme, e.g., human heparanase, hormone, receptor, immunoglobulin, structural protein and the like. Cells transformed with a chimeric construct as herein described are grown under suitable culturing conditions and the protein of interest (the polypeptide) is extracted therefrom or from the growth medium to which it is secreted.

According to still an additional aspect of the present invention there is provided a recombinant protein comprising a polypeptide (a) which is at least 75% similar to SEQ ID NO:4 or a portion thereof as determined using the BESTFIT™ software of the Wisconsin sequence analysis package, utilizing the Smith and Waterman algorithm, where gap weight equals 8 and length weight equals 2, average match equals 2.912 and average mismatch equals −2.003; (b) encoded by a nucleic acid including a genomic, complementary or composite polynucleotide sequence being at least 65% identical to SEQ ID NO:10 or a portion thereof as determined using the BESTFIT™ software of the Wisconsin sequence analysis package, utilizing the Smith and Waterman algorithm, where gap weight equals 50, length weight equals 3, average match equals 10 and average mismatch equals −9; (c) encoded by a nucleic acid as set forth in SEQ ID NO:10 or a portion thereof; and/or encoded by a nucleic acid including a genomic, complementary or composite polynucleotide sequence being hybridizable with SEQ ID NO:10 or a portion thereof under hybridization conditions of hybridization solution containing 10% dextrane sulfate, 1 M NaCl, 1% SDS and 5×10$^6$ cpm $^{32}$p labeled probe, at 65° C., with a final wash solution of 1×SSC and 0.1% SDS and final wash at 65° C.

Thus, this aspect of the present invention encompasses (i) a polypeptide as set forth in SEQ ID NO:4; (ii) fragments thereof; (iii) polypeptides similar (identical+homologous acids) thereto; and (iv) altered polypeptides characterized by mutations, such as deletion, insertion or substitution of one or more amino acids, either naturally occurring or man induced, either randomly or in a targeted fashion.

According to further features in preferred embodiments of the invention described below, the polypeptide has heparanase catalytic activity or the polypeptide is cleavable by a protease so as to have the heparanase catalytic activity.

The recombinant protein of the present invention may be purified by any conventional protein purification procedure close to homogeneity and/or be mixed with additives. The recombinant protein may be manufactured using any of the genetically modified cells described above, which include any of the expression nucleic acid constructs described herein. The recombinant protein may be in any form. It may be in a crystallized form, a dehydrated powder form or in solution. The recombinant protein may be useful in obtaining pure heparanase, which in turn may be useful in eliciting anti-heparanase antibodies, either poly or monoclonal antibodies, and as a screening active ingredient in an anti-heparanase inhibitors or drugs screening assay or system.

According to a further aspect of the present invention there is provided a pharmaceutical composition comprising, as an active ingredient, the recombinant protein of described herein and a pharmaceutically acceptable carrier.

The heparanase according to the present invention can be administered to an organism per se, or in a pharmaceutical composition where it is mixed with suitable carriers or excipients.

As used herein a "pharmaceutical composition" refers to active or activatable heparanase, with other chemical components such as physiologically suitable carriers and excipients. The purpose of a pharmaceutical composition is to facilitate administration of an active ingredient to an organism.

Herein the term "active ingredient" refers to active or activatable heparanase accountable for a biological effect.

Hereinafter, the terms "physiologically acceptable carrier" and "pharmaceutically acceptable carrier" which may be interchangeably used refer to a carrier or a diluent that does not cause significant irritation to an organism and does not abrogate the biological activity and properties of the active ingredient.

Herein the term "excipient" refers to an inert substance added to a pharmaceutical composition to further facilitate administration of the active ingredient. Examples, without limitation, of excipients include calcium carbonate, calcium phosphate, various sugars and types of starch, cellulose derivatives, gelatin, vegetable oils and polyethylene glycols.

Techniques for formulation and administration of active ingredients may be found in "Remington's Pharmaceutical Sciences," Mack Publishing Co., Easton, Pa., latest edition, which is incorporated herein by reference.

Suitable routes of administration may, for example, include oral, rectal, transmucosal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the active ingredient in a local rather than systemic manner, for example, via injection of the active ingredient directly into a solid tumor often in a depot or slow release formulation, such as described below.

Furthermore, one may administer the active ingredient in a targeted drug delivery system, for example, in a liposome coated with a tumor specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredient into preparations which, can be used pharmaceutically. Proper formulation is dependent upon the route of administration chosen.

For injection, the active ingredient of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For administration by inhalation, the active ingredient for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

The active ingredient described herein may be formulated for parenteral administration, e.g., by bolus injection or continues infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredient may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredient to allow for the preparation of highly concentrated solutions.

Alternatively, the active ingredient may be in powder form for constitution with a suitable vehicle, e.g., sterile, pyrogen-free water, before use.

The active ingredient of the present invention may also be formulated for local administration, such as a depot preparation. Such long acting formulations may be administered by implantation (for example subcutaneously or intramuscularly) or by intramuscular injection. Thus, for example, the preparation may be formulated with suitable polymeric or hydrophobic materials (for example, as an emulsion in an acceptable oil) or ion exchange resins, or as sparingly soluble derivatives such as sparingly soluble salts. Formulations for topical administration may include, but are not limited to, lotions, suspensions, ointments gels, creams, drops, liquids, sprays emulsions and powders.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount the active ingredient effective to prevent, alleviate or ameliorate symptoms of disease or prolong the survival of the subject being treated.

Determination of a therapeutically effective amount is well within the capability of those skilled in the art, especially in light of the detailed disclosure provided herein.

The therapeutically effective amount or dose can be estimated initially from cell culture assays. For example, a dose can be formulated in animal models to achieve a circulating concentration range that includes the $IC_{50}$ as determined in cell culture. Such information can be used to more accurately determine useful doses in humans.

Toxicity and therapeutic efficacy of the active ingredient described herein can be determined by standard pharmaceutical procedures in cell cultures or experimental animals, e.g., by determining the $IC_{50}$ and the $LD_{50}$ (lethal dose causing death in 50% of the tested animals) for the active ingredient. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition.

The present invention can be used to develop treatments for various diseases, to develop diagnostic assays for these diseases and to provide new tools for basic and directed research especially in the fields of medicine and biology.

Specifically, the present invention can be used to develop new drugs to inhibit tumor cell metastasis, inflammation and autoimmunity. The identification of the hpa gene encoding for the heparanase enzyme from avian enables the production of a recombinant enzyme in heterologous expression systems.

Furthermore, the present invention can be used to modulate bioavailability of heparin-binding growth factors, cellular responses to heparin-binding growth factors (e.g., bFGF, VEGF) and cytokines (e.g., IL-8), cell interaction with plasma lipoproteins, cellular susceptibility to viral, protozoa and some bacterial infections, and disintegration of neurodegenerative plaques. Recombinant heparanase offers a potential treatment for wound healing, angiogenesis, restenosis, atherosclerosis, inflammation, neurodegenerative diseases (such as, for example, Genstmann-Straussler Syndrome, Creutzfeldt-Jakob disease, Scrape and Alzheimer's disease) and certain viral and some bacterial and protozoa infections. Recombinant heparanase can be used to neutralize plasma heparin, as a potential replacement of protamine.

As used herein, the term "modulate" includes substantially inhibiting, slowing or reversing the progression of a disease, substantially ameliorating clinical symptoms of a disease or condition, or substantially preventing the appearance of clinical symptoms of a disease or condition. A "modulator" therefore includes an agent which may modulate a disease or condition. Modulation of viral, protozoa and bacterial infections includes any effect which substantially interrupts, prevents or reduces any viral, bacterial or protozoa activity and/or stage of the virus, bacterium or protozoon life cycle, or which reduces or prevents infection by the virus, bacterium or protozoon in a subject, such as a human or lower animal.

As used herein, the term "wound" includes any injury to any portion of the body of a subject including, but not limited to, acute conditions such as s thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, those injuries sustained in automobile and other mechanical accidents, and those caused by bullets, knives and other weapons, and post-surgical injuries, as well as chronic conditions such as pressure sores, bedsores, conditions related to diabetes and poor circulation, and all types of acne, etc.

The present invention successfully addresses the shortcomings of the presently known configurations by providing novel polynucleotides which encode novel polypeptides having heparanase catalytic activity and which can be used to intervene with pathological procedures associated with impaired heparin-binding growth factors, cellular responses to heparin-binding growth factors and cytokines, cell interaction with plasma lipoproteins, cellular susceptibility to viral, protozoa and bacterial infections or disintegration of neurodegenerative plaques, all as is further delineated in the background section above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Culture of Animal Cells—A Manual of Basic Technique" by Freshney, Wiley-Liss, N.Y. (1994), Third Edition; "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND EXPERIMENTAL PROCEDURES

Cells

The methylcholanthrene-induced non-metastatic Eb (L5178Y) T-lymphoma cells (clone 737) were provided by V. Schirrmacher (DKFZ, Heidelberg, Germany). The cells were routinely transplanted as ascites tumors in syngeneic female DBA2/J mice. Alternatively, they were grown in RPMI 1640 (Life Technologies Inc., Rockville, Md., USA) supplemented with β-mercaptoethanol ($5 \times 10^{-5}$ M) and 10% FCS. C6 rat Glioma cells were obtained from Dr. E. Keshet (Hadassah Medical School Jerusalem Israel). Cells were cultured in DMEM (4.5 g glucose/liter) containing 10% fetal calf serum. Cells were dissociated with a solution of 0.05% trypsin, 0.02% EDTA, 0.01 M sodium phosphate, pH 7.4 and were subcultured at a 'split' ratio of 1:10.

Heparanase Activity

Cell lysates, intact cells, conditioned media and serum free conditioned media were incubated 24 hours at 37° C., pH 6.2–6.6, with $^{35}$S-labeled ECM in the presence of 20 mM phosphate buffer (pH 6.2). The incubation medium was centrifuged and the supernatant was analyzed by gel filtration on a SEPHAROSE CL-6B™ column (0.9×30 cm). Fractions (0.2 ml) were eluted with PBS and their radioactivity was measured. Nearly intact HSPGs was eluted next to just after the $V_0$ ($K_{av}$<0.2, peak I, fractions 1–10) whereas degradation fragments of HS side chains were eluted from SEPHAROSE CL-6B™ at 0.5<$K_{av}$<0.8 (peak II, fractions 15–35.

Cloning of Chk-hpa cDNA

The amino acid sequence of human heparanase was used to screen EST databases for homology to a chicken unidentified mRNA sequences. Following extensive searches, a single chicken derived EST suspected as heparanase related was identified, which shared only 60.5% sequence homology with a 276 bp nucleotide stretch at the 3' end of the human heparanase coding sequence. The full-length chicken heparanase cDNA was isolated from chicken kidney mRNA. To this end, mRNA was isolated from fresh chicken kidney using POLYATract™ mRNA Isolation System III (Promega, USA). The method for amplification of 5' ends was developed according to the principle of the 5' RACE SYSTEM™ (rapid amplification of cDNA ends) System of GibcoBRL. Chicken kidney mRNA was reverse transcribed (RT) using SuperScript II™ (Gibco BRL) and oligo $dT_{(15)}$ (SEQ ID NO:5) as a primer. Following RT the cDNA was extended by 3' C-tailing using terminal deoxynucleotidyl transferase (TdT) (Promega). PCR amplification used EXPAND HIGH FIDELITY™ enzyme (Boehringer). The primers used for amplification were:

First step: 5' primer, complementary to the C tail: AP1
 5'-GGCCACGCGTCGACTAGTACGGGIIGGGIIG GGIIG-3' SEQ ID NO:6 and the 3' gene specific primer ChkL1: 5'-GACTCCTCAAGCATTCCCTCAG-3' (SEQ ID NO:7). Second cycle: 5' nested primer nested AP2: 5'-GGCCACGCGTCGACTAGTACG-3' (SEQ ID NO:8) and a nested, gene specific 3' primer ChkL2 5'-AGCCCTGTTACTCTGCGTGCTC-3' (SEQ ID NO:9). The gene specific primers ChkL1 and ChkL2 were selected according to the sequence of the EST.

PCR program of both first and second cycles was as follows: 94° C. 3 minutes, followed by 30 cycles of: 94° C. 30 seconds, 64° C. 1 minute and 72° C. 3 minutes, and finally 72° C., 7 minutes.

The resulting 1.8-kb PCR product was cloned into the pGEM-T EASY VECTOR™ (Promega, USA).

DNA Sequencing

Sequence determination used vector-specific and gene-specific primers, with an automated DNA sequencer (ABI PRISM™ model 310 Genetic Analyzer). Each nucleotide was read from at least two independent primers, and from several clones.

Computer Analysis of Sequence

Database searches for sequence similarities were performed using the NCBI Blast network service. Sequence analysis and alignment of DNA and protein sequences were done using the DNA sequence analysis software package developed by the Genetic Computer Group (GCG) at the University of Wisconsin. Multiple alignment was generated by ClustalW.

Immunostaining

Cells were seeded on round cover slips in 4 well plates for 24 hours. Cell were then washed with PBS, fixed with 100% chilled (−20° C.) MetOH for 3 minutes. Following fixation cells were washed with PBS 5 times and intrinsic fluorescence was blocked with 50 mM $NH_4Cl$ for 5 minutes. Cells were washed with PBS 3 times, incubated with 5% goat serum for 30 minutes and washed with PBS twice. Slides were then incubated with anti heparanase monoclonal antibody HP-130, 8 µg/ml for 2 hours at room temperature, washed with PBS 5 times and then incubated with the second antibody Cy-3 conjugated goat anti mouse IgG (Jackson) for 1 hour at room temperature. Slides were washed with PBS 8 times, and mounting solution (90% glycerol in PBS) was added. The monoclonal antibody HP-130 was generated against human heparanase as described in U.S. patent application Ser. No. 08/922,170.

Generation of a Chimeric Chicken-human Heparanase Gene

The N-terminal coding portion of the human hpa (H-hpa) cDNA encoding the signal peptide was replaced by a corresponding sequence of the chicken hpa cDNA. To this end, the Chk-hpa signal peptide coding sequence was amplified using specific primers (KPN/SPU: 5'-CGGGGTACCCGATGCTGGTGCT-3' (SEQ ID NO:11); SPL: 5'-AGGTCCACGACGTCCTGTGCCGTC CGCCTCG-3', (SEQ ID NO:12)). A H-hpa cDNA region encoding a segment extending from the first amino acid downstream the H-hpa signal peptide to the BamHI restriction site was amplified, using H-hpa specific primers (HU: 5'-CGAGGCGGACGGCACAGGACGTCGTGGACCT-3' (SEQ ID NO:13; H/BHIL: 5'-CCACATCAGGAGGGATGGATCC-3' (SEQ ID NO:14). The PCR products were combined by means of primer extension and PCR amplification. The resulting fragment was then cloned in frame into a pCDNA3 plasmid (Invitrogen, NV Leek, Netherlands) containing the H-hpa cDNA downstream the BamHI site, generating a chimeric construct in which the Chk-hpa signal peptide precedes the H-hpa. The chimeric gene was validated by sequencing. SEQ ID NO:15 deleniates the chimeric cDNA, whereas SEQ ID NO:16 deleniates the amino acid sequence of the chimeric heparanase protein.

EXPERIMENTAL RESULTS

Failures in Cloning the Chicken Heparanase cDNA

Cloning of chicken heparanase was attempted based on minute homology to human heparanase. cDNA library of chicken kidney was screened using low stringency hybridization conditions and human hpa cDNA as a probe. No specific hybridization signal was observed and no hpa homologous clones could be isolated following the screening. A different approach utilized PCR primers of human hpa for amplification of the heparanase cDNA from chicken kidney. Human hpa primers failed to amplify chicken heparanase using annealing temperature as low as 37° C.

Cloning the Chicken Heparanase cDNA

The human heparanase amino acid sequence was used to screen EST databases for homology to a chicken unidentified mRNA sequences. Following extensive screening, a single related chicken EST was identified which shared 60.5% homology with the 276 bp at the 3' end of the human heparanase coding sequence. This sequence encoded a truncated open reading frame of 91 amino acids, 74% homologous to human heparanase, followed by 325 nucleotides 3' untranslated region (UTR). The heparanase homologous sequence was derived from chicken activated T cells cDNA, clone pat.pk0039.c8.f 5', mRNA sequence, accession # AI980994.

In order to isolate a full length clone and to test whether it is indeed heparanase, chicken kidney mRNA was subjected to 5' RACE (rapid amplification of cDNA ends). The gene specific PCR primers were designed according to the EST described above. A DNA fragment of approximately 1,600 bp was obtained, partially overlapping with the identified 3' encoding EST clone. The entire cDNA cloned, in pGEM-T EASY VECTOR™, was designated Chk-hpa. The complete cDNA (Chk-hpa) is 1,609 bp long (SEQ ID NO:10, FIG. 1b), and it contains an open reading frame that encodes a polypeptide of 523 amino acids (SEQ ID NO:4, FIGS. 1a–b) with a calculated molecular weight of 58,842 Daltons. Analysis of the amino acid sequence and of the hydropathic profile of the protein indicates a hydrophobic amino acid tail (FIG. 1a underlined) at the N-terminus. A signal peptide is predicted to span the N-terminal 19 amino acids.

The overall homology between the chicken and the human hpa coding sequences is 62%. The similarity between the chicken and the human heparanases is 69% (of which 61% amino acid sequence identity). The heparanase is synthesized as a latent, 65 kDa precursor and is then processed to an active mature 50 kDa form. Based on the homology to human heparanase the chicken heparanase is cleaved between $Trp^{136}$ and $Lys^{137}$. According to Fairbank et al. (57) the precursor is cleaved at three sites to form a heterodimer of a 50 kDa polypeptide (the mature form) that is associated with a 8 kDa peptide. The putative chicken 8 kDa peptide spans amino acids $Glu^{10}$ to $Glu^{94}$ (FIG. 1a). The mature heparanases of various organisms share high homology while the pro-peptides are relatively diverse (FIG. 1a).

Structure prediction of human heparanase suggests a $(\alpha/\beta)8$ Tim barrel fold typical of family 10 glycosyl hydrolases. According to this prediction the active site involves two glutamic acid residues, which are the proton donor and the nucleophile, with an asparagine always preceding the proton donor. The proton donor in human heparanase is $Glu^{225}$ and the nucleophile is $Glu^{343}$. The conservation of the amino acid sequence flanking these residues supports the identification of the active site. Based on the homology the proton donor of chicken heparanase is $Glu^{204}$ and the nucleophile is $Glu^{323}$.

The comparison between the nucleotide as well as the amino acid sequences of the all the heparanases published so far is presented in FIG. 6. Chicken heparanase is slightly more similar to human heparanase than to mouse and rat heparanases. As expected, the homology among mammals is far higher than that of mammals with chicken.

It is therefore yet to be determined whether the polynucleotide isolated from chicken indeed encodes a protein having heparanase catalytic activity. This is shown below.

Functional Expression of Recombinant Chicken Heparanase in Mammalian Cells

The ability of the Chk-Hpa product to catalyze degradation of heparan sulfate (HS) in vitro was determined by expressing the entire open reading frame of Chk-hpa in mammalian cells lacking heparanase activity. Mouse Eb-lymphoma and rat C6-glioma cells were transfected with the pcDNA3 plasmid vector containing the chicken heparanase cDNA (Chk-hpa) or with a control empty plasmid (mock transfected). Stable transfectants were then selected for further analysis. Expression of heparanase in the transfected cells was confirmed by RT-PCR. Chicken heparanase transcript was detected only in Chk-hpa transfected cells.

Heparanase activity was assayed in cells transfected with Chk-hpa as compared to mock transfected cells. As shown in FIGS. 3a–c high activity was observed in intact cells, conditioned media and cell lysates of Chk-hpa transfectants while no activity was observed in the mock transfected cells.

The heparan sulfate degradation activity of Eb cells transfected with Chk-hpa cDNA was compared with that of Eb cells transfected with human hpa (Hum-hpa). As shown in FIGS. 3a–c the activity of chicken heparanase was higher than that of human heparanase in intact cells and in conditioned media, however, in cell extracts the activity of the two enzymes was similar. This suggests that the chicken heparanase is unexpectedly preferentially secreted.

In order to compare the activity of the chicken and human heparanases, the enzymes were partially purified from conditioned media of Chk-hpa and Hum-hpa transfected cells. Western blot analysis of the partially purified chicken heparanase showed a major protein of 58 kDa, which corresponds to the heparanase precursor and a minor protein of 45 kDa, which corresponds to the mature form. The human heparanase fraction contained the equivalent human 65 kDa heparanase precursor and 50 kDa mature forms (FIG. 2). The difference in molecular weight between chicken and human heparanases is mainly due to a different glycosylation pattern.

Activity of the two enzymes was compared using equal amounts of the partially purified enzymes in a semi-quantitative assay. As shown in FIG. 4 the specific activity of chicken and human heparanases is similar.

Localization of Chicken Heparanase in Transfected Cells

Figures 5A, 5B, 5C, 5D:
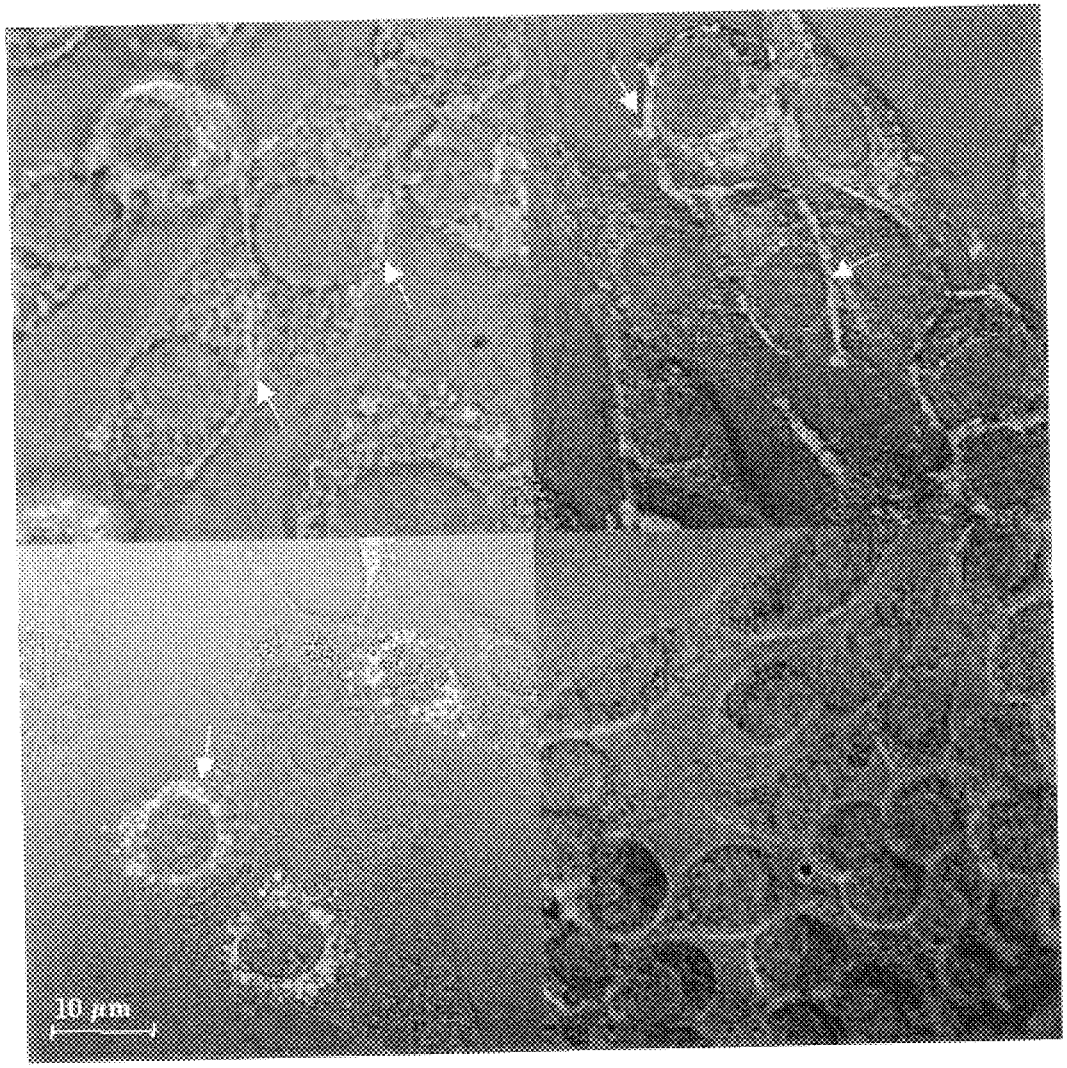

C-6 glioma cells stably transfected with the chicken or human heparanase cDNAs were grown in four well chamber slides and were subjected to indirect immunofluorescence staining with the anti-human heparanase mAb 130 (15). These antibodies cross-react with the chicken enzyme. Confocal fluorescence microscopy revealed that C-6 glioma cells transfected with the Chk-hpa cDNA exhibited an intense granular staining of the heparanase protein mostly associated with the cell surface. Preferential localization of the chicken heparanase was noted in areas of cell to cell contacts (FIG. 5a, arrow). Unlike this pattern of immunostaining, C-6 glioma cells overexpressing the human heparanase displayed primarily a peri-nuclear granular staining pattern with almost no detectable surface localization of the enzyme (FIG. 5c). A similar pattern was observed in transiently transfected human primary fibroblasts, where chicken heparanase was associated with cell membrane while human heparanase was localized to peri-nuclear vesicles, which were identified as lysosomes. The chicken and human heparanase cDNAs were also expressed in homologous cells (i.e., QT6 quail fibrosarcoma and Huh7 human hepatocarcinoma cells, respectively), resulting in an immunostaining pattern similar to that observed with the transfected C-6 rat glioma cells.

The signal peptides of the chicken and human heparanases share no significant homology. It appears that the signal peptide of chicken heparanase targets the enzyme to the cell surface of mammalian cells while the signal peptide of human heparanase targets the enzyme to lysosomes.

One may take advantage of the unexpected membrane targeting feature of chicken heparanase signal peptide for targeting other proteins to cell membrane.

Chimeric Chicken-human Heparanase Gene

The results described above indicate that the chicken heparanase is more readily secreted into the incubation medium and/or retained on the cell surface, as compared with the human enzyme, most likely due to the marked difference between the respective signal peptide sequences. In order to further study this unexpected observation, a chimeric construct was generated, composed of the chicken signal peptide fused to the human cDNA downstream nucleotide 105. Briefly, chicken specific primers were used to amplify the chicken signal sequence which was then fused by means of primer extension to the human hpa sequence, replacing its signal peptide, as described in Experimental Procedures above. The chimeric construct was subcloned into pcDNA3 plasmid which was then used to stable transfect Eb mouse lymphoma and C-6 rat glioma cells. Serum free medium conditioned for 24 hours by Eb cells transfected with the chimeric construct (chimeric-hpa, SEQ ID NOs:15 and 16) was tested for heparanase activity. As shown in FIG. 7, cells transfected with the chimeric enzyme were comparable to cells transfected with Chk-hpa in their ability to secrete the heparanase enzyme into the culture medium. In contrast, little or no heparanase activity was detected in medium conditioned by H-hpa transfected cells (FIG. 7), indicating that secretion of the enzyme is in fact driven by the chicken signal peptide sequence. Similar results were obtained with C-6 glioma cells.

Cellular Localization of Chimeric Heparanase Enzymes

The cell surface targeting of the chicken heparanase signal peptide was also demonstrated by the cellular localization of chimeric heparanase. Immunostaining of C-6 glioma cells transfected with the chimeric heparanase revealed preferential surface localization pattern (FIG. 5b), similar to that of cells expressing the chicken heparanase (5a). Mock transfected glioma cells showed no staining (FIG. 5d). The results of the swapping experiment emphasize that the pronounced difference in cellular localization of the chicken and human heparanases is due primarily to the marked difference in sequence, length and hydrophobic properties of the respective signal peptides. The preferential cell surface association of the chicken and chimeric heparanases is in accordance with the higher HS degrading activity expressed by intact cells overexpressing the chicken or chimeric enzymes vs. the human heparanase.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Durand, P., Lehn, P., Callebaut, I., Fabrega, S., Henrissat, B. and Mornon, J. P. (1997). Active-site motifs of lysosomal acid hydrolases: invariant features of clan GH-A glycosyl hydrolases deduced from hydrophobic cluster analysis. Glycobiology, 7(2), 277–284.
2. Vlodavsky, I., Friedmann, Y., Elkin, M., Aingorn, H., Atzmon, R., Ishai-Michaeli, R., Bitan, M., Pappo, O., Peretz, T., Michal, I., Spector, L and Pecker I. (1999). Mammalian heparanase: gene cloning, expression and function in tumor progression and metastasis. Nature Medicine (In press)
3. Wight, T. N., Kinsella, M. G., and Qwarnstromn, E. E. (1992). The role of proteoglycans in cell adhesion, migration and proliferation. Curr. Opin. Cell Biol., 4, 793–801.
4. Jackson, R. L., Busch, S. J., and Cardin, A. L. (1991). Glycosaminoglycans: Molecular properties, protein interactions and role in physiological processes. Physiol. Rev., 71, 481–539.
5. Wight, T. N. (1989). Cell biology of arterial proteoglycans. Arteriosclerosis, 9, 1–20.
6. Kjellen, L., and Lindahl, U. (1991). Proteoglycans: structures and interactions. Annu. Rev. Biochem., 60, 443–475.
7. Ruoslahti, E., and Yamaguchi, Y. (1991). Proteoglycans as modulators of growth factor activities. Cell, 64, 867–869.
8. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.
9. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.
10. Vlodavsky, I., Eldor, A., Haimovitz-Friedman, A., Matzner, Y., Ishai-Michaeli, R., Levi, E., Bashkin, P., Lider, O., Naparstek, Y., Cohen, I. R., and Fuks, Z. (1992). Expression of heparanase by platelets and circulating cells of the immune system: Possible involvement in diapedesis and extravasation. Invasion & Metastasis, 12, 112–127.
11. Nakajima, M., Irimura, T., and Nicolson, G. L. (1988). Heparanase and tumor metastasis. J. Cell. Biochem., 36, 157–167.
12. Vlodavsky, I. et al. Invasion Metastasis 1995, 14:290–302.
13. Nakagima, M. et al J. Cell. Biochem. 1988, 36:157–167.
14. Vlodavsky, I. et al. Cancer res. 1983, 43:2704–2711.
15. Vlodavsky, I. et al. J. Med 1988, 24:464–470.
16. Vlodavsky, I. et al. Invasion and Metastasis 12:112–127.
17. Gilat, D. et al. J. Exp. Med. 1995, 181:1929–1934.

18. Matzner et al. 1985, J. Clin. Invest. 10:1306–1313.
19. Mollinedo, F. et al. Biochem. J. 1997, 327:917–923.
20. Murphy, G. et al. Biochem. J. 1990, 192:517–525.
21. Nakajima, M. et al. J. Cell. Biochem. 1988, 36(2):157–167.
22. Ishai-Michaeli R. wt al. Cell Reg. 1990, 1:833–842.
23. Cardon-Cardo C. et al. Lab. Inrest. 1990, 63:832–840.
24. Nicolson, G. L. (1988). Organ specificity of tumor metastasis: Role of preferential adhesion, invasion and growth of malignant cells at specific secondary sites. Cancer Met. Rev., 7, 143–188.
25. Liotta, L. A., Rao, C. N., and Barsky, S. H. (1983). Tumor invasion and the extracellular matrix. Lab. Invest., 49, 639–649.
26. Vlodavsky, I., Fuks, Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. Cancer Res., 43, 2704–2711.
27. Sun L, Feusi E, Sibalic A, Beck-Schimmer B, Wuthrich R P (1998). expression profile of hyaluronidase mRNA transcripts in the kidney and in renal cells. Kidney Blood Press Res; 21(6):413–8
28. Parish, C. R., Coombe, D. R., Jakobsen, K. B., and Underwood, P. A. (1987). Evidence that sulphated polysaccharides inhibit tumor metastasis by blocking tumor cell-derived heparanase. Int. J. Cancer, 40, 511–517.
29. Burgess, W. H., and Maciag, T. (1989). The heparin-binding (fibroblast) growth factor family of proteins. Annu. Rev. Biochem., 58, 575–606.
30. Folkman, J., and Klagsbrun, M. (1987). Angiogenic factors. Science, 235, 442–447.
31. Vlodavsky, I., Folkman, J., Sullivan, R., Fridman, R., Ishai-Michaelli, R., Sasse, J., and Klagsbrun, M. (1987). Endothelial cell-derived basic fibroblast growth factor: Synthesis and deposition into subendothelial extracellular matrix. Proc. Natl. Acad. Sci. USA, 84,2292–2296.
32. Folkman, J., Klagsbrun, M., Sasse, J., Wadzinski, M., Ingber, D., and Vlodavsky, I. (1980). A heparin-binding angiogenic protein-basic fibroblast growth factor—is stored within basement membrane. Am. J. Pathol., 130, 393–400.
33. Bashkin, P., Doctrow, S., Klagsbrun, M., Svahn, C. M., Folkman, J., and Vlodavsky, I. (1989). Basic fibroblast growth factor binds to subendothelial extracellular matrix and is released by heparitinase and heparin-like molecules. Biochemistry, 28, 1737–1743.
34. Ishai-Michaeli, R., Svahn, C.-M., Chajek-Shaul, T., Korner, G., Ekre, H.-P., and Vlodavsky, I. (1992). Importance of size and sulfation of heparin in release of basic fibroblast factor from the vascular endothelium and extracellular matrix. Biochemistry, 31, 2080–2088.
35. Ishai-Michaeli, R., Eldor, A., and Vlodavsky, I. (1990). Heparanase activity expressed by platelets, neutrophils and lymphoma cells releases active fibroblast growth factor from extracellular matrix. Cell Reg., 1, 833–842.
36. Vlodavsky, I., Bar-Shavit, R., Ishai-Michaeli, R., Bashkin, P., and Fuks, Z. (1991). Extracellular sequestration and release of fibroblast growth factor: a regulatory mechanism? Trends Biochem. Sci., 16, 268–271.
37. Vlodavsky, I., Bar-Shavit, R., Korner, G., and Fuks, Z. (1993). Extracellular matrix-bound growth factors, enzymes and plasma proteins. In Basement membranes: Cellular and molecular aspects (eds. D. H. Rohrbach and R. Timpl), pp 327–343. Academic press Inc., Orlando, Fla.
38. Yayon, A., Klagsbrun, M., Esko, J. D., Leder, P., and Ornitz, D. M. (1991). Cell surface, heparin-like molecules are required for binding of basic fibroblast growth factor to its high affinity receptor. Cell, 64, 841–848.
39. Spivak-Kroizman, T., Lemmon, M. A., Dikic, I., Ladbury, J. E., Pinchasi, D., Huang, J., Jaye, M., Crumley, G., Schlessinger, J., and Lax, I. (1994). Heparin-induced oligomerization of FGF molecules is responsible for FGF receptor dimerizatio, activation, and cell proliferation. Cell, 79, 1015–1024.
40. Ornitz, D. M., Herr, A. B., Nilsson, M., West, a., J., Svahn, C.-M., and Waksman, G. (1995). FGF binding and FGF receptor activation by synthetic heparan-derived di- and trisaccharides. Science, 268, 432–436.
41. Gitay-Goren, H., Soker, S., Vlodavsky, I., and Neufeld, G. (1992). Cell surface associated heparin-like molecules are required for the binding of vascular endothelial growth factor (VEGF) to its cell surface receptors. J. Biol. Chem., 267, 6093–6098.
42. Ernst S, Langer R, Cooney C. L., Sasisekharan R. (1995). Enzymatic degradation of glycosaminoglycans. Crit Rev Biochem Mol Biol; 30(5):387–444
43. Current protocols in molecular biology (1994–1999). Ausubel, F. M., Brent, R., Kingston, R. E., Moore D. D., Seidman, J. G., Smith, J. A., Struhl, K. Eds. John Wiley & Sons, Inc.
44. Rapraeger, A., Krufka, A., and Olwin, B. R. (1991). Requirement of heparan sulfate for bFGF-mediated fibroblast growth and myoblast differentiation. Science, 252, 1705–1708.
45. Shieh, M-T., Wundunn, D., Montgomery, R. I., Esko, J. D., and Spear, P. G. J. (1992). Cell surface receptors for herpes simplex virus are heparan sulfate proteoglycans. J Cell Biol., 116, 1273–1281.
46. Chen, Y., Maguire, T., Hileman, R. E., Fromm, J. R., Esko, J. D., Linhardt, R. J., and Marks, R. M. (1997). Dengue virus infectivity depends on envelope protein binding to target cell heparan sulfate. Nature Medicine 3, 866–871.
47. Putnak, J. R., Kanesa-Thasan, N., and Innis, B. L. (1997). A putative cellular receptor for dengue viruses. Nature Medicine 3, 828–829. Narindrasorasak, S., Lowery, D., Gonzalez-DeWhitt, P., Poorman, R. A., Greenberg, B., Kisilevsky, R. (1991). High affinity interactions between the Alzheimer's beta-amyloid precursor protein and the basement membrane form of theparan sulfate proteoglycan. J. Biol. Chem., 266, 12878–83.
49. Eisenberg, S., Sehayek, E., Olivecrona, T., and Vlodavsky, I. (1992). Lipoprotein lipase enhances binding of lipoproteins to heparan sulfate on cell surfaces and extracellular matrix. J. Clin. Invest., 90, 2013–2021.
50. Ross, R. (1993). The pathogenesis of atherosclerosis: a perspective for the 1990s. Nature (Lond.)., 362:801–809.
51. Zhong-Sheng, J., Walter, J., Brecht, R., Miranda, D., Mahmood Hussain, M., Innerarity, T. L. and Mahley, W. R. (1993). Role of heparan sulfate proteoglycans in the binding and uptake of apolipoprotein E-enriched remnant lipoproteins by cultured cells. J. Biol. Chem., 268, 10160–10167.
52. Current protocols in protein science (1996–1999). Coligan, J. E., Dunn, B. M., Ploegh, H. L., Speicher, D. W. and Wingfield, P. T. Eds. John Wiley & Sons Inc.
53. Freeman C and Parish C R (1998) Human platelet heparanase: purification, characterization and catalytic activity. : *Biochem J Mar* 15;330 (Pt 3):1341–50.
54. Kussie et al. (1999) Biochem Biophys Res Commun. 261(1):183–7.
55. Hullet et al. (1999) Nature Medicine 5(7):803–809.
56. Toyoshima and Nakajima (1999). J. Biol. Chem. 274 (34):24153–24160.
57. Fairbanks et al. (1999) J. Biol. Chem. 274(42):29587–29590.
58. Friedmann et al. (2000) Am J Pathol (in press).

What is claimed is:

1. An isolated nucleic acid comprising a genomic, complementary or composite polynucleotide sequence encoding a polypeptide being at least 75% similar to SEQ ID NO:4 as determined using the BESTFIT™ software of the Wisconsin sequence analysis package, utilizing the Smith and Waterman algorithm, where gap weight equals 8 and length weight equals 2, average match equals 2.912 and average mismatch equals −2.003, wherein said polypeptide has heparanase catalytic activity or said polypeptide is cleavable by a protease so as to have said heparanase catalytic activity.

2. An isolated nucleic acid comprising a genomic, complementary or composite polynucleotide sequence being at least 75% identical to SEQ ID NO:10 as determined using the BESTFIT™ software of the Wisconsin sequence analysis package, utilizing the Smith and Waterman algorithm, where gap weight equals 50, length weight equals 3, average match equals 10 and average mismatch equals −9, wherein said polynucleotide encodes a polypeptide which has heparanase catalytic activity or which is cleavable by a protease so as to have said heparanase catalytic activity.

3. An isolated nucleic acid as set forth in SEQ ID NO:10.

4. An isolated nucleic acid comprising a genomic, complementary or composite polynucleotide sequence being hybridizable with SEQ ID NO:10 under hybridization conditions of hybridization solution containing 10% dextrane sulfate, 1 M NaCl, 1% SDS and 5×10$^6$ cpm $^{32}$p labeled probe, at 65° C., with a final wash solution of 1×SSC and 0.1% SDS and final wash at 65° C. and wherein said polynucleotide encodes a polypeptide which has heparanase catalytic activity or which is cleavable by a protease so as to have said heparanase catalytic activity.

5. A nucleic acid construct comprising the isolated nucleic acid of claim 1.

6. A nucleic acid construct comprising the isolated nucleic acid of claim 3.

7. A nucleic acid construct comprising the isolated nucleic acid of claim 6.

8. A cell transformed or transfected with the nucleic acid of claim 1.

9. A cell transformed or transfected with the nucleic acid of claim 2.

10. A cell transformed or transfected with the nucleic acid of claim 4.

11. A nucleic acid construct comprising a first polynucleotide encoding a peptide as set forth at positions 1 to 19 of SEQ ID NO:4 and an in frame, second polynucleotide encoding a membrane targeted or secreted polypeptide.

12. The nucleic acid construct of claim 11, wherein said membrane targeted or secreted polypeptide is human heparanase.

13. A method of expressing a protein of interest in a cell, the method comprising:

transforming the cell with a nucleic acid construct that comprises a first polynucleotide encoding a signal peptide of avian or reptile heparanase as set forth in positions 1–19 of SEQ ID NO:4 and an in frame, second polynucleotide encoding a membrane targeted or secreted polypeptide; and ulturing the cell.

14. An isolated nucleic acid comprising a polynucleotide sequence encoding a polypeptide as set forth in SEQ ID NO:4.

15. A nucleic acid construct comprising the isolated nucleic acid of claim 14.

16. A cell transformed with the nucleic acid of claim 14.

* * * * *

UNITED STATES PATENT AND TRADEMARK OFFICE
CERTIFICATE OF CORRECTION

PATENT NO. : 6,677,137 B2
DATED : January 13, 2004
INVENTOR(S) : Goldshmidt et al.

It is certified that error appears in the above-identified patent and that said Letters Patent is hereby corrected as shown below:

<u>Title page,</u>
Item [73], Assignees, should read

-- [73] Assignees: Insight Strategy & Marketing Ltd., Rehovot (IL);
 Hadasit Medical Research and Development Ltd.,
 Jerusalem (IL). --

Signed and Sealed this

Thirteenth Day of April, 2004

JON W. DUDAS
*Acting Director of the United States Patent and Trademark Office*